United States Patent
Morizumi et al.

(10) Patent No.: US 9,507,141 B2
(45) Date of Patent: Nov. 29, 2016

(54) STEREOSCOPIC ENDOSCOPE DEVICE

(71) Applicant: FUJIFILM Corporation, Tokyo (JP)

(72) Inventors: Masaaki Morizumi, Ashigarakami-gun (JP); Shuji Ono, Ashigarakami-gun (JP); Seiichi Watanabe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 323 days.

(21) Appl. No.: 14/147,211

(22) Filed: Jan. 3, 2014

(65) Prior Publication Data

US 2014/0210945 A1    Jul. 31, 2014

(30) Foreign Application Priority Data

Jan. 25, 2013 (JP) .................. 2013-012356

(51) Int. Cl.
| | |
|---|---|
| A61B 1/04 | (2006.01) |
| G02B 23/24 | (2006.01) |
| A61B 1/00 | (2006.01) |
| A61B 1/045 | (2006.01) |
| A61B 1/05 | (2006.01) |

(52) U.S. Cl.
CPC ....... *G02B 23/2415* (2013.01); *A61B 1/00096* (2013.01); *A61B 1/00188* (2013.01); *A61B 1/00193* (2013.01); *A61B 1/045* (2013.01); *A61B 1/05* (2013.01)

(58) Field of Classification Search
CPC ................... H04N 2005/2255; H04N 5/2255; H04N 13/0203; A61B 1/00193
See application file for complete search history.

(56) References Cited

U.S. PATENT DOCUMENTS 5,557,454 A * 9/1996 Takahashi .......... A61B 1/00193
                                                        348/45
5,907,434 A * 5/1999 Sekine ................ H04N 5/2259
                                                        348/335

FOREIGN PATENT DOCUMENTS

| JP | 2001-66513 A | 3/2001 |
|---|---|---|
| JP | 2003-334160 A | 11/2003 |

* cited by examiner

*Primary Examiner* — Christopher Findley
(74) *Attorney, Agent, or Firm* — Birch, Stewart, Kolasch & Birch, LLP

(57) ABSTRACT

Provided is a stereoscopic endoscope device enabling precise observation based on a 3D-image and observation of a wide field of view range based on a 2D-image and enabling the change of the field of view range according to the situation with a simple structure without increasing the size of an imaging unit or complicating the configuration. An imaging unit 50 disposed in a distal portion of a stereoscopic endoscope includes a pair of left and right imaging units 50L, 50R that capture a parallax image of a subject of a part of interest. The left and the right imaging unit 50L, 50R include a left and a right imaging optical system 60L, 60R, which form a subject image, and reflecting mirrors 302L and 302R located on the rear end sides of the left and the right imaging optical system 60L, 60R, respectively.

22 Claims, 15 Drawing Sheets (C) ENDOSCOPE IMAGE IR&IL (B) LEFT IMAGE IL          (A) RIGHT IMAGE IR (C) ENDOSCOPE IMAGE IR&IL (B) LEFT IMAGE IL (A) RIGHT IMAGE IR (C) ENDOSCOPE IMAGE IR&IL (B) LEFT IMAGE IL (A) RIGHT IMAGE IR

STEREOSCOPIC ENDOSCOPE DEVICE

BACKGROUND OF THE INVENTION

1. Field of the Invention

The present invention relates to a stereoscopic endoscope device, and in particular, to a stereoscopic endoscope device that captures a parallax image using an imaging unit, which is provided in a distal portion of an insertion unit inserted into the body cavity, so that a stereoscopic image (3D image) of a subject body part in the body cavity can be displayed.

2. Description of the Related Art

A stereoscopic endoscope device includes a pair of left and right imaging units (imaging means) including an imaging optical system and a solid state imaging element, which are provided in a distal portion of an insertion unit of the endoscope device inserted into the body cavity. A subject body part is imaged by the imaging units, and left and right parallax images are obtained as a stereoscopic image (3D image) for stereoscopic viewing. In addition, the 3D image is 3D displayed by a 3D display device such that a right-eye image is observed by the right eye of the observer and a left-eye image is observed by the left eye of the observer. As a result, the subject body part is observed stereoscopically.

In the stereoscopic endoscope device, neither the situation of a portion near the subject body part nor the position of the treatment instrument can be checked only by the observation of the subject body part based on the 3D image. For this reason, JP2003-334160A (JP-H15-334160A) discloses that not only an imaging unit for capturing a 3D image (referred to as a 3D imaging unit herein) but also an imaging unit for capturing a wide-angle 2D image for plan view (referred to as a 2D imaging unit herein) is provided.

In addition, JP2003-334160A (JP-H15-334160A) and JP2001-66513A (JP-H13-66513A) disclose that the 3D imaging unit has a zoom function.

SUMMARY OF THE INVENTION

According to JP2003-334160A (JP-H15-334160A), precise observation based on a 3D image that is suitable, for example, when observing a lesion part or when treating a part to be treated using a treatment instrument and observation of a wide field of view range based on a 2D image that is suitable, for example, at the time of orienting when guiding an endoscope or a treatment instrument to a part to be treated or the like or when checking the treatment situation or the like are possible.

In JP2003-334160A (JP-H15-334160A), however, since the 2D imaging unit is provided separately from the 3D imaging unit, there are many problems in terms of an increase in the number of components, the degree of difficulty of assembly, accuracy control, and the like. In addition, since many optical elements are provided, there is also a problem of a dark screen.

In addition, since the 3D imaging unit and the 2D imaging unit are not coaxial optical system, the deviation of the center of the field of view and the change in the relationship of the front and rear positions occur. As a result, the positional relationship cannot be displayed correctly. Therefore, when the 3D image and the 2D image are displayed so as to be switchable therebetween, there is a problem in that the center of the screen moves sensuously. This may lead to a determination error.

In addition, when it is possible to change the field of view range according to the zoom magnification of the zoom optical system of the 3D imaging unit as disclosed in JP2001-66513A (JP-H13-66513A), there is no choice but to increase the magnification change of the zoom optical system for the demand to image a wider field of view range, in particular, for the intention to increase the field of view range by simply moving the observation field of view range in a horizontal direction. This causes an increase in the size of the 3D imaging unit. On the other hand, it is difficult to increase the magnification change of the zoom optical system due to the limitation of the size of the endoscope. Accordingly, it is not easy to increase the field of view range.

The present invention has been made in view of the above described situation, and it is an object of the present invention to provide a stereoscopic endoscope device that enables precise observation based on a 3D image and observation of a wide field of view range based on a 2D image and enables the change of the field of view range according to the situation with a simple structure without increasing the size of an imaging unit or complicating the configuration.

In order to achieve the above-mentioned object, a stereoscopic endoscope device according to an aspect of the present invention is a stereoscopic endoscope that has an imaging optical system, which forms a subject in a direction of an observation axis that is an observation direction of the subject, as a subject image, along left and right optical paths disposed symmetrically with respect to the observation axis and that acquires a pair of left and right parallax images for stereoscopic viewing. The stereoscopic endoscope device includes: an imaging system that includes a pair of left and right imaging elements that have light receiving surfaces, on which images are formed by the imaging optical system, and are integrally movable along the direction of the observation axis, the light receiving surfaces of the pair of left and right imaging elements being disposed in parallel to the observation axis and symmetrically with respect to the observation axis; optical path change means for changing an optical path so that the pair of left and right optical paths face the light receiving surfaces of the pair of left and right imaging elements, respectively; and field of view range change means for shifting a field of view range of each of the pair of left and right imaging elements in a left and right direction by moving the pair of left and right imaging elements in the direction of the observation axis.

According to this aspect, since the light receiving surfaces of the pair of left and right imaging elements can be moved in a direction along the image surface of the subject image formed by the imaging optical system, the field of view ranges of the pair of left and right imaging elements can be shifted in opposite directions of the left and right directions. In this case, in the field of view ranges of the pair of left and right imaging elements, a field of view range in which the field of view ranges overlap each other and field of view ranges, which are located on both sides of the field of view range in the horizontal direction and in which the field of view ranges do not overlap each other, are generated. As a result, a subject image of the former field of view range can be acquired as a 3D image and subject images of the latter field of view ranges can be acquired as 2D images.

Therefore, precise observation based on the 3D image and observation of a wide field of view range based on the 2D images are possible. In addition, the sizes of the field of view ranges can be changed by the movement of the imaging elements according to the situation.

In addition, since both the imaging elements can be moved in the direction of the observation axis, the present invention can be implemented without increasing the size of the imaging unit. In addition, since both the imaging elements are integrally moved, the present invention can be implemented without complicating the configuration compared with a case where the imaging elements are separately moved.

In a stereoscopic endoscope device according to another aspect of the present invention, in the imaging system, the light receiving surfaces of the pair of left and right imaging elements may be disposed in opposite directions. This aspect is a form related to the arrangement of the light receiving surfaces that is made possible by disposing the light receiving surfaces of the imaging elements in parallel to the observation axis, and in particular, is a configuration suitable for the miniaturization of an observation unit.

In a stereoscopic endoscope device according to still another aspect of the present invention, in the imaging system, the light receiving surfaces of the pair of left and right imaging elements may be disposed so as to face each other. This aspect is another form related to the arrangement of the light receiving surfaces that is made possible by disposing the light receiving surfaces of the imaging elements in parallel to the observation axis.

In a stereoscopic endoscope device according to still another aspect of the present invention, in the imaging system, the pair of left and right imaging elements may be integrally supported by a substrate on which a circuit is mounted.

In a stereoscopic endoscope device according to still another aspect of the present invention, the field of view range change means may move the pair of left and right imaging elements in the direction of the observation axis by power of a motor connected to the imaging system. This aspect is a form for moving the imaging elements in the direction of the observation axis by power.

In a stereoscopic endoscope device according to still another aspect of the present invention, the field of view range change means may move the pair of left and right imaging elements in the direction of the observation axis by power transmitting an operating wire connected to the imaging system. This aspect is a form in which the imaging elements can also be moved in the direction of the observation axis manually (by manual force).

In a stereoscopic endoscope device according to still another aspect of the present invention, a front lens for setting a convergence angle may be further provided on a subject side of the imaging optical system.

According to this aspect, since the convergence angle is set by the front lens, it is not necessary to set the convergence angle by tilting the optical axes of the left and right optical systems after the front lens. This is advantageous when forming an optical system in the narrow space of the endoscope.

In a stereoscopic endoscope device according to still another aspect of the present invention, 3D image generation means for generating an image of a region, in which field of view ranges of the pair of left and right parallax images overlap each other, as a 3D image for stereoscopic viewing and generating an image of a region, in which the field of view ranges do not overlap each other, as a 2D image for plan view for extending the left and right sides of the 3D image may be further provided.

According to this aspect, a 3D image and a 2D image can be displayed simultaneously, and precise observation based on the 3D image and observation of a wide field of view range based on the 2D image are possible.

In a stereoscopic endoscope device according to still another aspect of the present invention, the 3D image generation means may reduce brightness of an image in a boundary region between the 3D image and the 2D image.

According to this aspect, it is possible to reduce the discomfort due to the collapse of three-dimensional recognition in a boundary region between the 3D image and the 2D image when displaying the 2D image by extending the left and right sides of the 3D image.

In a stereoscopic endoscope device according to still another aspect of the present invention, 2D image generation means for generating an image of a full field of view range of the pair of left and right parallax images as a 2D image for plan view may be further provided. This is advantageous since the full field of view range of the pair of left and right parallax images can also be displayed as a 2D image by displaying the image of the region, in which the field of view ranges of a pair of left and right parallax images overlap each other, as a 2D image as in the aspect.

In a stereoscopic endoscope device according to still another aspect of the present invention, the 2D image generation means may generate an image of a region in which field of view ranges of the pair of left and right parallax images overlap each other, as a 3D image that is not stereoscopically viewable, by thinning processing. This aspect is a form for displaying an image of a region, in which the field of view ranges overlap each other, as a 2D image when displaying the full field of view range of the pair of left and right parallax images as a 2D image, and a 2D image can be displayed without changes to the case where a 3D image is displayed.

In a stereoscopic endoscope device according to still another aspect of the present invention, the 2D image generation means may generate an image of a region in which field of view ranges of the pair of left and right parallax images overlap each other, as a 2D image, by combination processing.

This is another form for displaying an image of a region, in which the field of view ranges overlap each other, as a 2D image when displaying the full field of view range of the pair of left and right parallax images as a 2D image in the stereoscopic endoscope device according to still another aspect of the present invention. In this case, a 2D image can be generated by combining a pair of left and right parallax images unlike the aspect described above.

According to the present invention, it is possible to perform precise observation based on a 3D image and observation of a wide field of view range based on a 2D image and make a change to an appropriate field of view range according to the situation with a simple structure without increasing the size of an imaging unit or complicating the configuration.

DESCRIPTION OF THE PREFERRED EMBODIMENTS

Hereinafter, preferred embodiments of the present invention will be described in detail with reference to the accompanying drawings.

Figure 1:
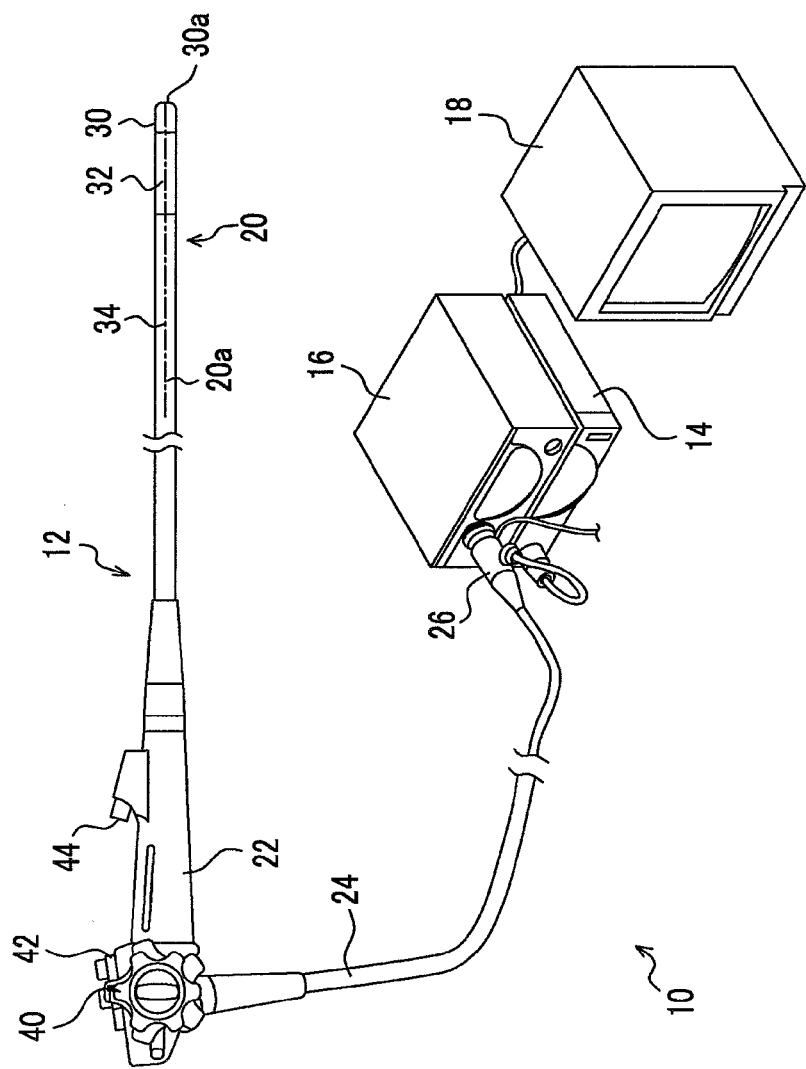
FIG. 1 is an overall configuration diagram showing the outline of the appearance of a stereoscopic endoscope system to which the present invention is applied.

FIG. 1 is an overall configuration diagram showing the outline of the appearance of a stereoscopic endoscope system (stereoscopic endoscope device) to which the present invention is applied. A stereoscopic endoscope system 10 shown in FIG. 1 is a system that can capture and display a stereoscopic image (3D image) for stereoscopic viewing. Except for the configuration and processing relevant to imaging, the stereoscopic endoscope system 10 is not largely different from a known endoscope system that captures and displays a normal 2D image (image for plan view) instead of a 3D image. Hereinafter, the configuration and processing relevant to imaging will be mainly described, and it is assumed that other configuration and processing are similar to those of any known endoscope system.

As shown in FIG. 1, the stereoscopic endoscope system 10 of the present embodiment is configured to include a stereoscopic endoscope 12 (hereinafter, referred to as an endoscope 12), a processor device 14 and a light source device 16 to which the endoscope 12 is connected, a 3D display device 18 connected to the processor device 14, and the like.

The endoscope 12 is inserted into the body cavity of a patient, and a pair of left and right parallax images (a left image and a right image) for displaying a 3D image of a desired part of interest is captured by the endoscope 12. Illumination light supplied from the light source device 16 to the endoscope 12 is irradiated to a part of interest. In addition, these parallax images are used as images for displaying not only the 3D image but also a wide-angle 2D image.

The parallax images captured by the endoscope 12 are transmitted to the processor device 14, and are formed as display images for displaying a 3D image or a 2D image by required processing. Then, the display image is output to the 3D display device 18, so that the 3D image or the 2D image is displayed on the 3D display device 18 as an endoscope image. The practitioner can observe a subject body part in the body cavity in a two-dimensional or three-dimensional manner by observing the endoscope image displayed on the 3D display device 18.

Figure 2:
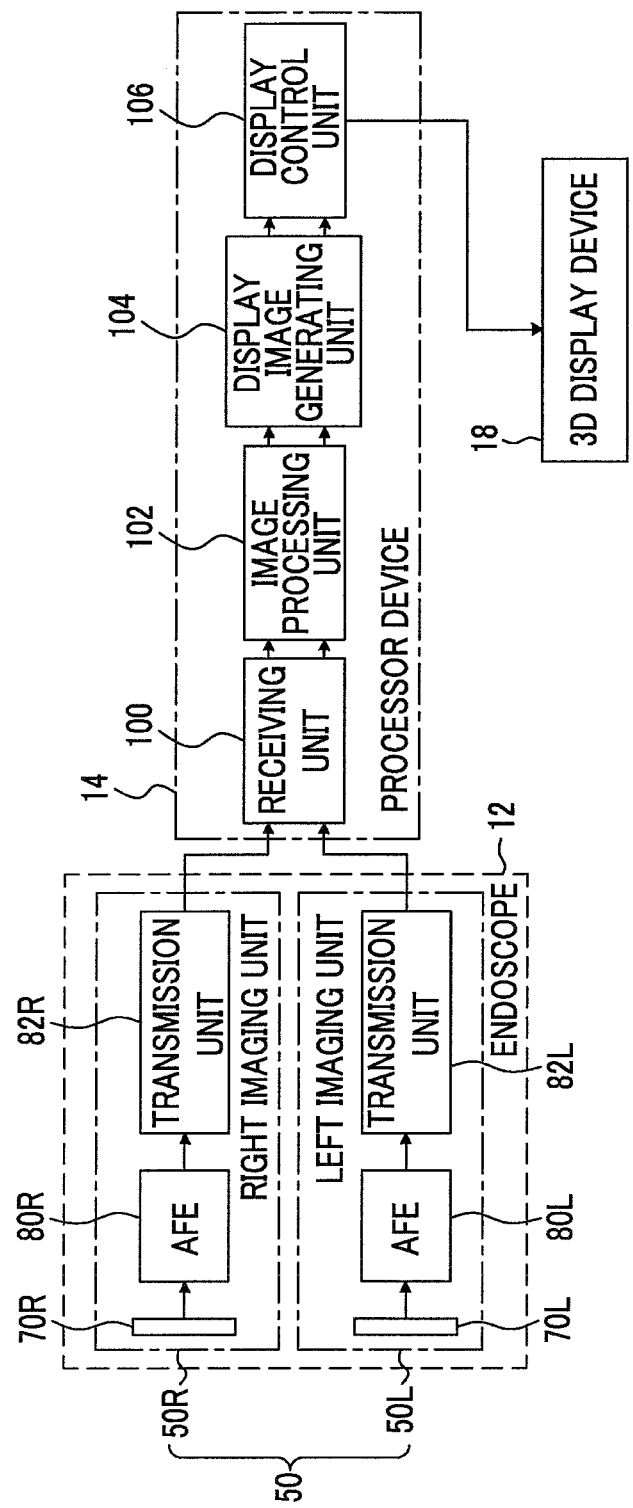
FIG. 2 is a block diagram showing the configuration relevant to processing units until parallax images captured by an endoscope are displayed on a 3D display device as endoscope images in the stereoscopic endoscope system.

FIG. 2 is a block diagram showing the configuration relevant to processing units until parallax images captured by the endoscope 12 are displayed on the 3D display device 18 as endoscope images in the above-described stereoscopic endoscope system 10.

As shown in FIG. 2, the endoscope 12 includes an imaging unit 50 that images a subject body part to acquire a pair of left and right parallax images of the part of interest, and the imaging unit 50 includes a pair of left imaging unit 50L and right imaging unit 50R, which will be described in detail later. Each of the left imaging unit 50L and the right imaging unit 50R includes an imaging optical system (not shown), image sensors 70L and 70R, analog signal processing units (AFE) 80L and 80R, transmission units 82L and 82R, and the like.

Subject light from the subject body part captured by the imaging unit 50 is formed as a light image (subject image) on the light receiving surfaces of the image sensors 70L and 70R through the imaging optical system (not shown) of each of the left imaging unit 50L and the right imaging unit 50R. Then, these subject images are captured (photoelectrically converted) as a pair of left and right parallax images by the image sensors 70L and 70R and are output, as imaging signals, from the image sensors 70L and 70R to the analog signal processing units (AFE) 80L and 80R. In addition, it is assumed that the parallax image acquired by the right imaging unit 50R is a right image and the parallax image acquired by the left imaging unit 50L is a left image.

The imaging signals input to the analog signal processing units (AFE) 80L and 80R are output as parallel digital signals from the AFEs 80L and 80R to the transmission units 82L and 82R after analog signal processing, such as correlation double sampling (CDS), automatic gain control (AGC), and analog/digital conversion (A/D).

The imaging signals input to the transmission units 82L and 82R are transmitted to a cable (signal line) connected to the imaging units 50R and 50L, as serial digital signals, after parallel/serial conversion processing and the like. The cable is inserted through an insertion unit 20, an operating unit 22, and a universal cord 24 and is connected to a receiving unit 100 of the processor device 14, and the imaging signal transmitted to the cable is received by the receiving unit 100.

Here, in the present embodiment, assuming that the endoscope image is displayed on the 3D display device 18 as a moving image, left and right images are continuously captured as frame images that form a moving image in the image sensors 70L and 70R, and the imaging signals of left and right images captured sequentially as frame images are sequentially transmitted from the transmission units 82L and 82R to the receiving unit 100 as serial digital signals for each frame image. When displaying an endoscope image on the 3D display device 18 as a still image, left and right images of one frame that forms a still image are captured in synchronization with the shutter release operation of the operator in the operating unit 22 of the endoscope 12 or an operating unit 324 of the processor device 14, and the imaging signals of these left and right images are transmitted from the transmission units 82L and 82R to the receiving unit 100 as serial digital signals.

In addition, in order to transmit the imaging signals from the transmission units 82L and 82R to the receiving unit 100, it is desirable to use a high-speed digital transmission technique in which data transmission is performed using a low voltage operating signal (LVDS), for example. In addition, the imaging signals of the left and right images may be transmitted in parallel using different signal lines, or may be transmitted alternately using a common signal line.

The processor device 14 includes the receiving unit 100, an image processing unit 102, a display image generating unit 104, a display control unit 106, and the like as a processing unit for displaying an endoscope image.

As described above, the imaging signals of the left and right images, which are transmitted as serial digital signals from the transmission units 82L and 82R of the imaging unit 50 of the endoscope 12 and received by the receiving unit 100 of the processor device 14, are subjected to parallel/serial conversion processing and the like. As a result, the imaging signals are restored to parallel digital signals before being converted in the transmission units 82L and 82R, and are output from the receiving unit 100 to the image processing unit 102.

The imaging signals input to the image processing unit 102 are subjected to digital image processing, such as color separation, color interpolation, gain correction, white balance adjustment, gamma correction, edge enhancement processing, and brightness adjustment processing. As a result, the imaging signals of the left and right images are generated as image data suitable for display or the like, and the image data is transmitted from the image processing unit 102 to the display image generating unit 104.

In addition, in the image processing unit 102, image data of the left and right images is sequentially generated, and the image data is temporarily stored in a memory (not shown) and is sequentially updated to latest image data. The latest image data is sequentially transmitted from the memory to the display image generating unit 104. Thus, the image data of the left and right images generated as described above can be used not only for displaying onto the 3D display device 18 but also for recording onto recording media, such as a hard disk and removable media.

The display image generating unit 104 acquires the image data of the left and right images generated by the image processing unit 102, and generates image data of a right-eye display image and a left-eye display image when displaying an endoscope image on the screen of the 3D display device 18 using the image data.

The right-eye display image and the left-eye display image are images displayed on the entire screen of the 3D display device 18, and indicate an image viewed only by the right eye and an image viewed only by the left eye of the observer who observes the screen of the 3D display device 18, respectively. The right image acquired from the image processing unit 102 forms an image of a region, which corresponds to the display position or the size on the screen, in the right-eye display image, and the left image forms an image of a region, which corresponds to the display position or the size on the screen, in the left-eye display image. In addition, other pieces of information (image data or character data), such as patient information or state information of the endoscope 12, can be added to the right-eye display image and the left-eye display image.

The image data of the right-eye display image and the left-eye display image generated by the display image generating unit 104 are sequentially updated with the update of the image data of the left and right images, and are output to the display control unit 106.

The image data of the right-eye display image and the left-eye display image input to the display control unit 106 are formed as a video signal for displaying the right-eye display image and the left-eye display image on the 3D display device 18, and the video signal is output from the display control unit 106 to the 3D display device 18.

As a result, on the screen of the 3D display device 18, an image (video) according to the video signal from the display control unit 106 is displayed, and is displayed such that the right-eye display image generated by the display image generating unit 104 is viewed by the right eye of the observer and the left-eye display image is viewed by the left eye of the observer. In addition, by the display and update of the endoscope image based on the left and right images included in the left-eye display image and the right-eye display image, the endoscope image is displayed as a moving image and a 3D image or a 2D image of a subject of the subject body part is displayed.

In addition, in the 3D display device 18, the subject of the subject body part captured by the endoscope 12 is displayed (3D displayed) as a 3D image by displaying the right image of the left and right images acquired from the endoscope 12 as an image within the right-eye display image, which is viewed only by the right eye of the observer, and displaying the left image as an image within the left-eye display image, which is viewed only by the left eye of the observer. In addition, by displaying an image of a subject, which is included in only one of the left and right images, similar to the 3D image, the image of the subject is displayed as a 2D image.

As the 3D display device 18 of the present embodiment, any arbitrary 3D display devices can be used. For example, it is possible to use known 3D display devices, such as a 3D display device based on a method in which a left-eye display image and a right-eye display image are alternately displayed on the screen of a monitor so that the left-eye display image is observed by the left eye and the right-eye display image is observed by the right eye through the shutter glasses that are opened and closed alternately in synchronization with the alternate display (frame sequential method), a 3D display device based on a method in which a left-eye display image and a right-eye display image are alternately displayed on the screen of a monitor, for example, in units of a scanning line so that the left-eye display image is observed by the left eye and the right-eye display image is observed by the right eye through the polarizing filter glasses having different polarization directions in the left and right (polarization method), a 3D display device based on a method in which a left-eye display image and a right-eye display image are displayed so that different images can be displayed according to an angle when viewing the screen by aligning microlenses on the screen of a monitor and accordingly the left-eye display image can be observed even by the naked left eye and the right-eye display image can be observed even by the naked right eye (integral imaging method), and a 3D display device based on a method in which a left-eye display image and a right-eye display image are displayed so that different images can be displayed according to an angle when viewing the screen by disposing a fine vertically-striped light blocking material on the screen of a monitor and accordingly the left-eye display image can be observed even by the naked left eye and the right-eye display image can be observed even by the naked right eye (parallax barrier method). In addition, it is also possible to use a 3D display device based on a method in which a left-eye display image and a right-eye display image are respectively displayed on two monitors for left and right eyes, such as a head mount display, so that the left-eye display image is observed by the left eye and the right-eye display image is observed by the right eye. In addition, a monitor to display a 2D image may also be provided separately from a monitor to display a 3D image as the 3D display device 18. In addition, in the present embodiment, the 3D display device 18 that uses a monitor is assumed.

Next, the configuration of the endoscope 12 shown in FIG. 1 will be described.

The endoscope 12 includes the insertion unit 20 that can be inserted into the body cavity of the patient (subject), the operating unit 22 that the practitioner grips to perform various operations, and the universal cord 24 that connects the endoscope 12 to the processor device 14 and the light source device 16.

The insertion unit 20 is formed in a long shape with a longitudinal axis 20a in the longitudinal direction as the central axis, and has an outer peripheral surface that is approximately circular in a cross-section perpendicular to the longitudinal axis 20a. The insertion unit 20 is formed by a distal portion 30, a curved portion 32, and a flexible portion 34.

The distal portion 30 is provided at the distal end of the insertion unit 20, and has a distal end surface 30a approximately perpendicular to the longitudinal axis 20a. In the distal portion 30, as will be described in detail later, a constituent component of the imaging unit 50 that images a subject body part in the body cavity located on the front side with respect to the distal end surface 30a, a constituent component of an illumination unit that emits illumination light from the light source device 16 to a subject body part imaged by the imaging unit 50, and the like are housed and held in a hard member.

The curved portion 32 is connected to the proximal side of the distal portion 30, and can be actively curved in all directions by the rotation operation of an angle knob 40 of the operating unit 22. By changing the direction of the distal portion 30 within the body cavity by an operation of curving the curved portion 32, it is possible to adjust a direction of a subject body part imaged by the imaging unit 50 of the distal portion 30.

The flexible portion 34 is connected to the proximal side of the curved portion 32 and the distal end of the operating unit 22, and makes a connection between the proximal end of the curved portion 32 and the distal end of the operating unit 22. The flexible portion 34 is soft and flexible. Since the flexible portion 34 is passively curved according to the shape of the path of insertion into the body cavity or the like, the distal portion 30 can be inserted and disposed at the desired position in the body cavity. A cable, a light guide, and the like connected to the imaging unit 50 or the illumination unit of the distal portion 30 are inserted through the flexible portion 34 and the curved portion 32.

The operating unit 22 is connected to the proximal side of the insertion unit 20, and operating members of the endoscope 12, such as the angle knob 40 or an air•water supply button 42, are provided in the operating unit 22. The practitioner can perform various operations of the endoscope 12 by gripping the operating unit 22 and operating the operating member provided in the operating unit 22.

In addition, a treatment instrument insertion port 44 is provided on the distal side of the operating unit 22. The treatment instrument insertion port 44 communicates with the distal portion 30 (treatment instrument outlet 54 to be described later) through a treatment instrument channel (pipeline) inserted through the insertion unit 20. Therefore, by inserting a desired treatment instrument through the treatment instrument insertion port 44, the treatment instrument is derived from the treatment instrument outlet 54 of the distal portion 30 so that treatment corresponding to the type of the treatment instrument can be performed on the treatment part in the body cavity.

The universal cord 24 extends from the operating unit 22, and a connector 26 of the composite type is provided at its end. The universal cord 24 is connected to the processor device 14 and the light source device 16 by the connector 26.

A cable, a light guide, and the like inserted through the insertion unit 20 and the operating unit 22 from the imaging unit 50 or the illumination unit of the distal portion 30 are inserted through the universal cord 24. The cable (signal line) connected to the imaging unit 50 is connected to the processor device 14 through the connector 26, and the light guide connected to the illumination unit is connected to the light source device 16 through the connector 26.

In this manner, imaging signals of parallax images (left and right images) captured by the imaging unit 50 of the distal portion 30 as described above are transmitted to the processor device 14 through the cable, and illumination light emitted from the light source device 16 is transmitted from the illumination unit of the distal portion 30 through the light guide.

Figure 3:
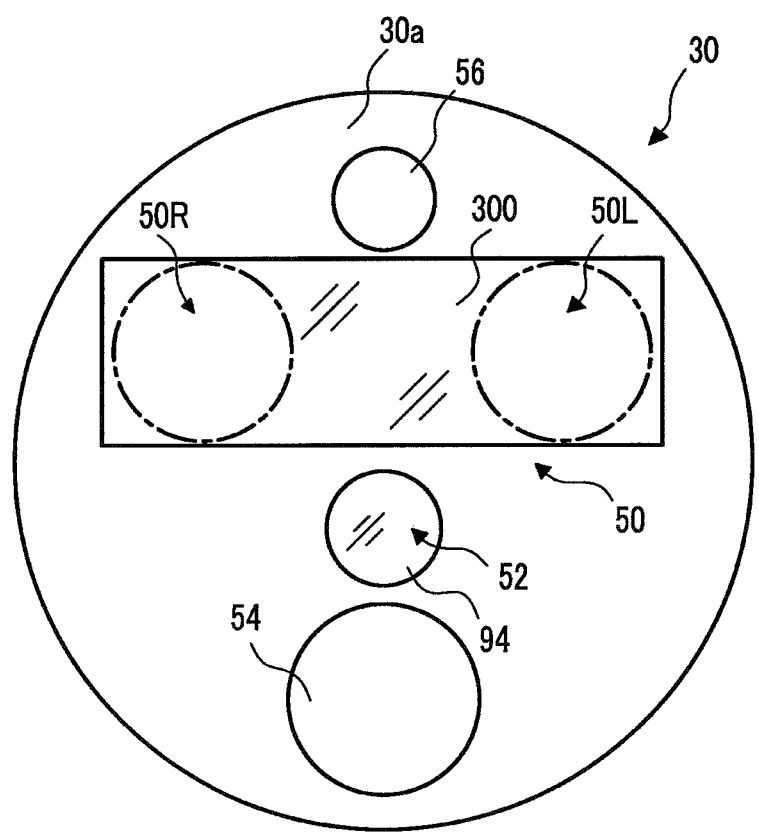
FIG. 3 is a front view of a distal portion of the endoscope when viewed from the distal end surface side.

FIG. 3 is a front view of the distal portion 30 of the endoscope 12 when viewed from the distal end surface 30a side. As shown in FIG. 3, the imaging unit 50 that images a subject body part on the front side of the distal end surface 30a and an illumination unit 52 that emits illumination light to illuminate a subject body part are disposed in the distal portion 30.

The imaging unit 50 has a pair of left imaging unit 50L and right imaging unit 50R provided side by side in a horizontal direction. By the left imaging unit 50L and the right imaging unit 50R, a pair of left and right images with parallax obtained by capturing the subject of the same part of interest in the body cavity from different positions are captured.

On the distal end surface 30a, a front lens 300 for making light from the subject of the subject body part being transmitted to each of the left imaging unit 50L and the right imaging unit 50R is disposed, and an illumination window 94 through which illumination light from the illumination unit 52 is emitted to the subject body part is disposed. In addition, the treatment instrument outlet 54 to derive a treatment instrument, which is inserted through the treatment instrument insertion port 44 of the insertion unit 20 and passes through the treatment instrument channel, from the distal end surface 30a and an air•water supply nozzle 56 to inject washing water or air toward the front lens 300 by the operation of the air•water supply button 42 of the operating unit 22 are provided on the distal end surface 30a.

Next, the configuration of the imaging unit 50 will be described.

Figure 4:
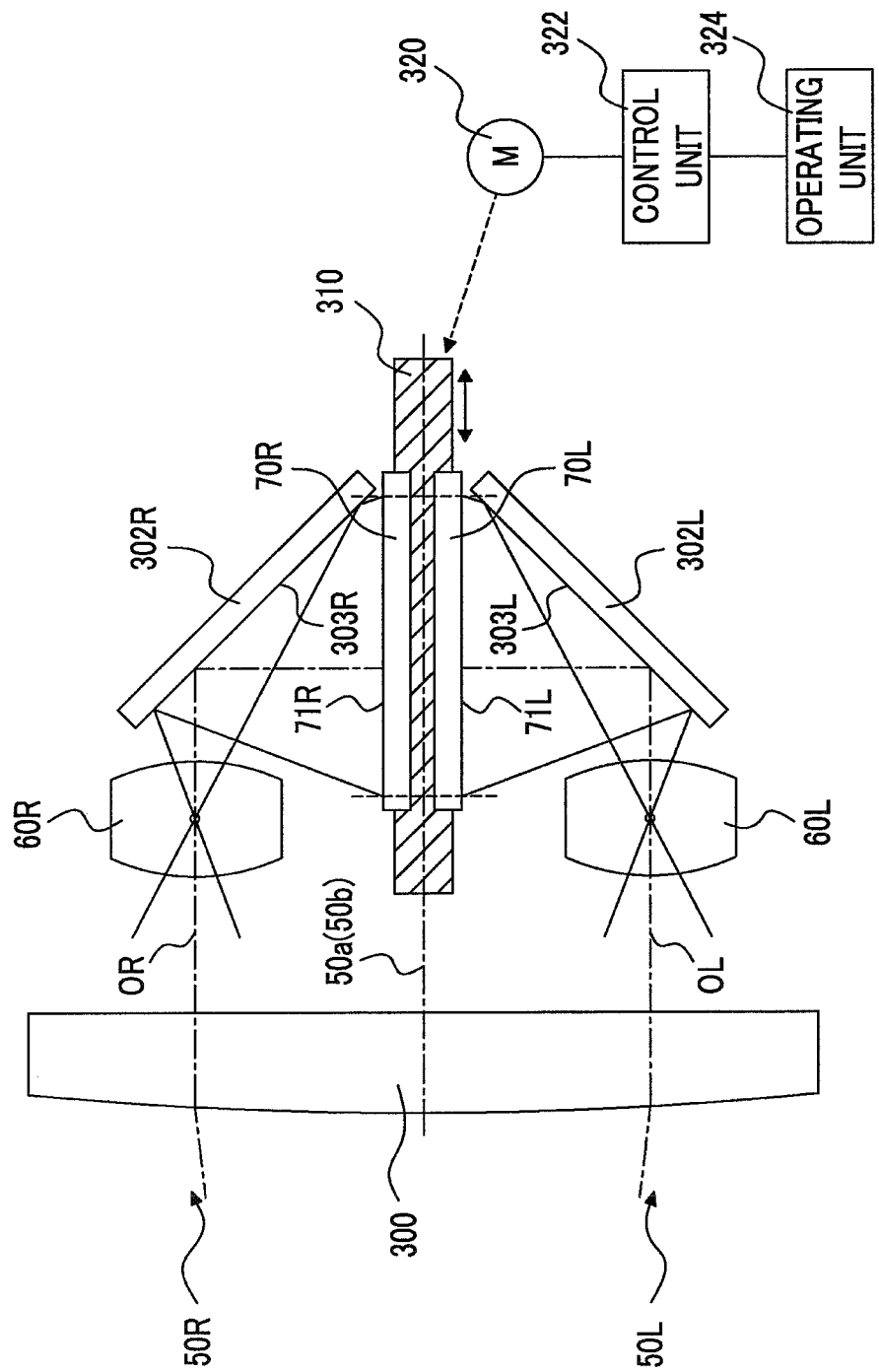
FIG. 4 is a cross-sectional view showing the configuration of imaging units in the endoscope.

FIG. 4 is a cross-sectional view showing the configuration of the imaging unit 50. As shown in FIG. 4, the imaging unit 50 is formed by the left imaging unit 50L and the right imaging unit 50R that are disposed symmetrically with respect to a central plane 50a perpendicular to the plane of the diagram as a horizontal plane (symmetrically with respect to a central axis 50b to be described later). In addition, the central plane 50a is a plane parallel to the longitudinal axis 20a of the insertion unit 20 in the endoscope 12. For example, in the present embodiment, the central plane 50a includes the longitudinal axis 20a. However, the imaging unit 50 may be disposed at a position shifted in the left and right direction from the center of the distal portion 30 as a whole, or may perform imaging in a direction different from the front side of the distal end surface 30a. It is not necessary for the longitudinal axis 20a to be included in central plane 50a.

The left imaging unit 50L and the right imaging unit 50R have the same structure except that they are horizontally reversed. The right imaging unit 50R includes: the front lens 300 shown in FIG. 3 that is shared by the left imaging unit 50L and the right imaging unit 50R; and a right imaging optical system 60R, a reflecting mirror 302R, and an image sensor 70R that are disposed, as constituent components of the right imaging unit 50R, in the distal portion 30 of the endoscope 12 after the front lens 300. The left imaging unit 50L includes: the front lens 300 shown in FIG. 3 that is shared by the left imaging unit 50L and the right imaging unit 50R; and a left imaging optical system 60L, a reflecting mirror 302L, and an image sensor 70L that are disposed, as constituent components of the left imaging unit 50L, in the distal portion 30 after the front lens 300. In addition, these constituent components of the left imaging unit 50L and the right imaging unit 50R corresponding to each other are disposed symmetrically with respect to the central plane 50a.

The front lens 300 is disposed on the distal end surface 30a of the distal portion 30 as shown in FIG. 3, and shields the opening of the distal end surface 30a through which subject light from the subject body part is transmitted into the distal portion 30.

In addition, the front lens 300 has a function as a convex lens (lens having a positive refractive power), and generates a convergence angle so that the cross point (intersection), at which the optical axis OL of the left imaging optical system 60L and the optical axis OR of the right imaging optical system 60R cross each other, is placed at a predetermined position.

Here, when the front lens 300 is not disposed, it is necessary to match the optical axis OL of the left imaging optical system 60L and the optical axis OR of the right imaging optical system 60R with the convergence angle. That is, it is necessary to tilt the optical axes OL and OR of the imaging optical systems according to the convergence angle to further secure a distance required as a distance between the optical axes OL and OR.

On the other hand, when the front lens 300 is disposed as in the present embodiment, the convergence angle can be determined by the design of the front lens 300. In addition, the left imaging optical system 60L and the right imaging optical system 60R after the front lens 300 can be disposed in parallel by securing only the distance between the optical axes OL and OR.

Therefore, this is very advantageous since design can be made while maintaining only the distance between the optical axes of left and right imaging optical systems and the convergence angle can be set by the front lens 300 when forming the imaging optical systems in a narrow space as the distal portion 30 of the insertion unit 20 of the endoscope 12.

In addition, such a front lens 300 shared by the left imaging unit 50L and the right imaging unit 50R is not necessarily required, and a foremost lens or a window member of each of the left imaging unit 50L and the right imaging unit 50R may be disposed at the position of the distal end surface 30a.

The left imaging optical system 60L and the right imaging optical system 60R are optical systems having the same characteristics that are formed by one or a plurality of lenses, and are supported within a lens barrel (not shown) in the distal portion 30 of the endoscope 12. In addition, the optical axes OR and OL are disposed so as to be approximately parallel to each other and to be parallel to the longitudinal axis 20a of the insertion unit 20. However, it is not necessary that the optical axes OR and OL are parallel to each other.

Subject light incident through the front lens 300 passes through the left imaging optical system 60L and the right imaging optical system 60R to form images. As a result, a subject image is formed on each of light receiving surfaces (imaging surfaces) 71L and 71R of the image sensors 70L and 70R.

In addition, when the line of intersection (that is, an observation axis as an observation direction of the imaging unit 50) between the horizontal plane (plane of the diagram) including the optical axes OR and OL and the central plane 50a is the central axis 50b of the imaging unit 50, the object side (subject side) of the imaging unit 50 in a direction along the central axis 50b is referred to as a forward direction and the opposite side is referred to as a backward direction. In the present embodiment, the optical axes OL and OR of the left imaging optical system 60L and the right imaging optical system 60R are parallel to the central axis 50b. When the reflecting mirrors 302L and 302R described below are not disposed, subject images are formed on a plane perpendicular to the central axis 50b by the left imaging optical system 60L and the right imaging optical system 60R.

In addition, although the left imaging optical system 60L and the right imaging optical system 60R are shown in a simplified manner as one lens in FIG. 4, the left imaging optical system 60L and the right imaging optical system 60R may be formed by a plurality of lenses and are not limited to having a specific configuration. In addition, the left imaging optical system 60L and the right imaging optical system 60R may be formed by one or a plurality of lenses, which are shared by the left imaging optical system 60L and the right imaging optical system 60R, instead of being formed by separate lenses.

The reflecting mirrors 302L and 302R are fixed to a lens barrel that supports the left imaging optical system 60L and a lens barrel that supports the right imaging optical system 60R, respectively, for example. In addition, the normal of each of reflecting surfaces 303L and 303R of light is parallel to the horizontal plane (plane of the diagram), and the normal of the reflecting surface 303R is disposed at an angle of 45° counterclockwise with respect to the optical axis OR and the normal of the reflecting surface 303L is disposed at an angle of 45° clockwise with respect to the optical axis OL.

By these reflecting mirrors 302L and 302R, the optical axis OR of the right imaging optical system 60R is bent in a direction perpendicular to the central plane 50a toward the central plane 50a (central axis 50b) side, and the optical axis OL of the left imaging optical system 60L is bent in a direction perpendicular to the central plane 50a toward the central plane 50a side. In addition, subject light transmitted through each of the left imaging optical system 60L and the right imaging optical system 60R is reflected toward the central plane 50a. In addition, instead of the reflecting mirrors 302L and 302R, a reflector such as a prism having the same function may be used.

For example, the image sensors 70L and 70R are CCD or MOS type (CMOS) solid state imaging elements having the same characteristics, and are mounted on the top and bottom surfaces of a plate-shaped substrate 310 disposed in a direction along the central plane 50*a*. Therefore, the image sensors 70L and 70R are fixed to the substrate 310 back to back and are integrally supported.

In addition, the image sensors 70L and 70R are disposed in a manner such that the light receiving surfaces 71L and 71R are parallel to the central plane 50*a* (central axis 50*b*), and are also disposed in a manner such that the horizontal direction of the light receiving surfaces 71L and 71R is parallel to the horizontal plane (plane of the diagram) and the vertical direction of the light receiving surfaces 71L and 71R is a direction perpendicular to the horizontal plane (direction perpendicular to the plane of the diagram). In addition, the horizontal direction of the light receiving surfaces 71L and 71R indicates a direction when subject images formed on the light receiving surfaces 71L and 71R are in the horizontal direction (left and right direction) on parallax images captured by the image sensors 70L and 70R, and the vertical direction of the light receiving surfaces 71L and 71R indicates a direction perpendicular to the horizontal direction on the light receiving surfaces 71L and 71R.

The subject light transmitted through the left imaging optical system 60L and the right imaging optical system 60R and reflected toward the central plane 50*a* by the reflecting mirrors 302L and 302R as described above is incident on the light receiving surfaces 71L and 71R of the image sensors 70L and 70R and forms subject images on the light receiving surface 71L and 71R. Then, the subject images are photo-electrically converted (captured) by the image sensors 70L and 70R, and are acquired as a pair of left and right parallax images (left and right images).

The substrate 310 is formed in a plate shape having a fixed thickness, and is disposed in a manner such that the central position of the width in the thickness direction overlaps the position of the central plane 50*a*. Accordingly, the substrate 310 is disposed symmetrically with respect to the central plane 50*a*, and the light receiving surfaces 71L and 71R of the image sensors 70L and 70R are disposed at the same distance on the opposite sides with respect to the central plane 50*a*.

However, the shape and the arrangement of the substrate 310 are not limited thereto, and any shape or arrangement, in which the image sensors 70L and 70R are supported such that the light receiving surfaces 71L and 71R of the image sensors 70L and 70R are parallel to the central plane 50*a* at the same distance on the opposite sides with respect to the central plane 50*a*, may be adopted.

Not only the image sensors 70L and 70R but also required circuit components are mounted on the substrate 310, and wiring is performed so that signal lines (not shown) to transmit signals (imaging signals) of the parallax images acquired by the image sensors 70L and 70R and the like are connected to terminals (not shown). The signal lines are inserted through the insertion unit 20 of the endoscope 12, the operating unit 22, and the universal cord 24 and are connected to the processor device 14 through the connector 26, so that the processor device 14 can acquire the parallax images acquired by the image sensors 70L and 70R and the control of the image sensors 70L and 70R can be performed using a control signal from the processor device 14.

In addition, within the distal portion 30, the substrate 310 is supported so as to be movable in a direction of the central axis 50*b* (direction of the longitudinal axis 20*a* of the insertion unit 20), and the substrate 310 and the image sensors 70L and 70R are shifted as a unit in the direction of the central axis 50*b*, that is, in the horizontal direction of the light receiving surfaces 71L and 71R. Therefore, the light receiving surfaces 71L and 71R are shifted in the direction of the central axis 50*b*, that is, in the horizontal direction of the light receiving surfaces 71L and 71R.

In addition, as the light receiving surfaces 71L and 71R are shifted in the direction of the central axis 50*b*, a field of view range where each of the left imaging unit 50L and the right imaging unit 50R images a subject is also shifted in the horizontal direction (left and right direction).

A motor 320 mounted in the distal portion 30 of the endoscope 12 is connected to the substrate 310 so that power can be transmitted through a power transmission mechanism (not shown), and the substrate 310 is moved in the direction of the central axis 50*b* by the power of the motor 320. The motor 320 is connected to a control unit 322 mounted in the processor device 14 through the signal line, which is inserted through the insertion unit 20 of the endoscope 12, the operating unit 22, and the universal cord 24, and is controlled according to the control signal from the control unit 322.

In addition, not only the normal DC motor or the normal AC motor but also a general actuator that is driven by electric power, such as a voice coil motor (VCM) or a piezoelectric actuator, is included in the motor 320.

The operating unit 324 used when the operator inputs various kinds of information is provided in the processor device 14 (an input device connected to the processor device 14 as the operating unit 324 is also included), and information input from the operating unit 324 is transmitted to the control unit 322.

When the operator inputs instruction information regarding the shift of the field of view range of the imaging unit 50 (setting positions of the image sensors 70L and 70R) through the operating unit 324, the control unit 322 controls the motor 320 based on the instruction information and moves the substrate 310 in the direction of the central axis 50*b* so as to be set at a position based on the instruction information. Thus, the operator can shift the field of view range of each of the left imaging unit 50L and the right imaging unit 50R in the left and right direction by moving the image sensors 70L and 70R to desired positions within the movable range by operating the operating unit 324.

In addition, instruction information regarding the movement of the substrate 310 may be given by the operating unit 22 of the endoscope 12.

In addition, the substrate 310 may be moved in the direction of the central axis 50*b* by the power of the motor or manually through the operating wire connected to the substrate 310 instead of moving the substrate 310 in the direction of the central axis 50*b* by the power of the motor 320. For example, one end of an operating wire inserted through the insertion unit 20 is fixed to the substrate 310 and the other end of the operating wire is connected to an operating member, such as a swing lever, provided in the operating unit 22 of the endoscope 12, so that an operation of pushing or pulling the operating wire can be performed using the operating member.

Thus, the image sensors 70L and 70R can be set at desired positions in the direction of the central axis 50*b* by moving the substrate 310 in the direction of the central axis 50*b* by the operation of pushing or pulling the operating wire using the operating member. In addition, instead of the operation of pushing or pulling the operating wire using the operating member, the operating wire may be made to rotate and the rotational force may be transmitted as power to move the substrate 310 in the direction of the central axis 50*b*.

Next, the field of view range of the imaging unit 50 will be described.

Figure 5:
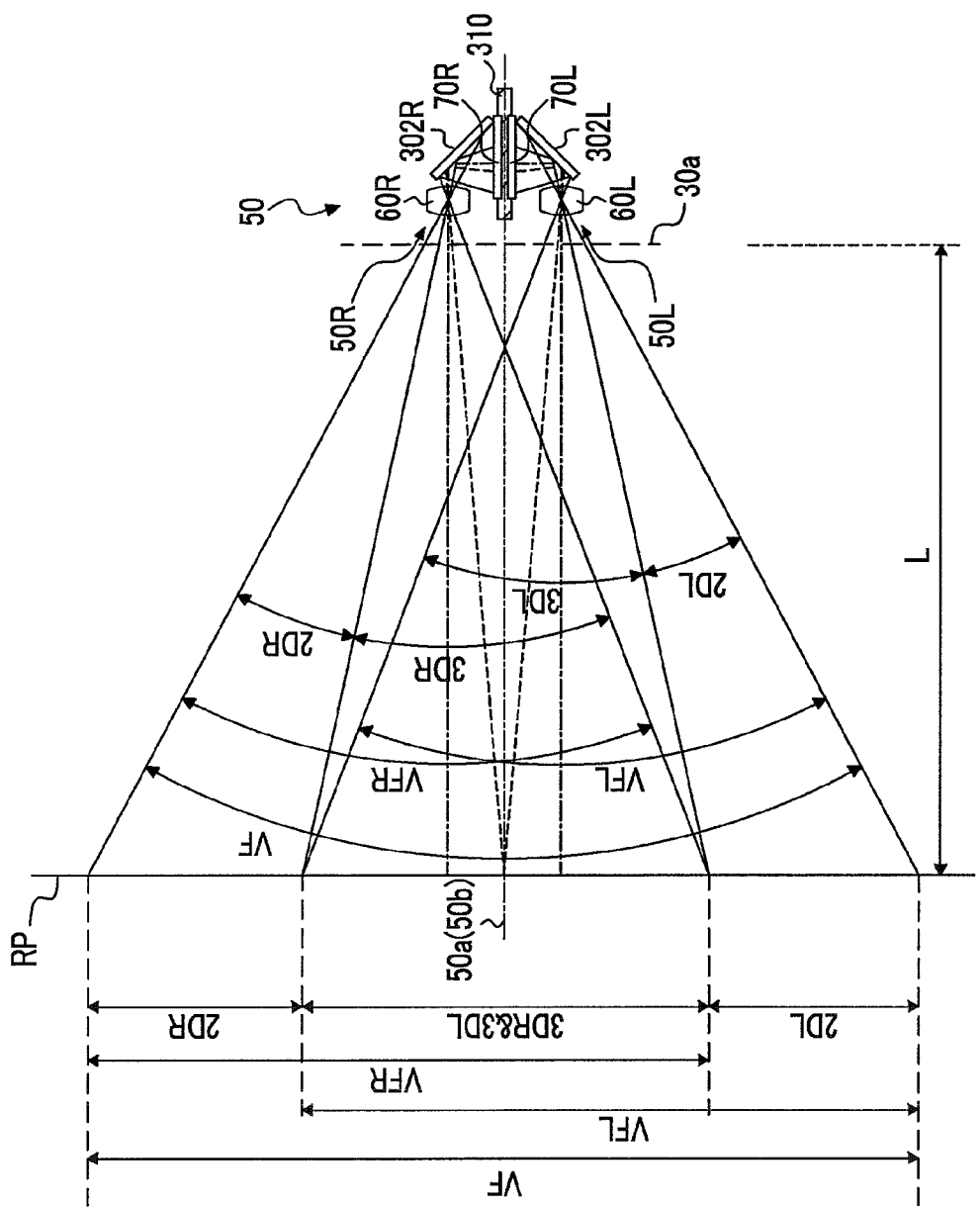
FIG. 5 is a diagram showing the field of view range of the imaging units shown in FIG. 4.

FIG. 5 is a diagram showing the field of view range of the imaging unit 50 shown in FIG. 4.

FIG. 5 shows the configuration of a field of view range of the imaging unit 50 in a state where the image sensors 70L and 70R are set at arbitrary positions of a movable range in the direction of central axis 50b. The field of view range where the right imaging unit 50R images a subject is indicated by VFR, and the field of view range where the left imaging unit 50L images a subject is indicated by VFL. The field of view range VFR and the field of view range VFL are symmetrical with respect to the central plane 50a and overlap each other in a central portion. In addition, the front lens 300 is omitted in FIG. 5.

A field of view range VF obtained by adding the field of view range VFR and the field of view range VFL, that is, the field of view range VF from the right end of the field of view range VFR to the left end of the field of view range VFL indicates the entire field of view range VF of the imaging unit 50 that is imaged by at least one of the left imaging unit 50L and the right imaging unit 50R.

In FIG. 5, a reference plane (observation setting plane) RP is a plane perpendicular to the central plane 50a (central axis 50b). In the present embodiment, the reference plane RP is also perpendicular to the longitudinal axis 20a of the insertion unit 20. In addition, the reference plane RP is located at a predetermined distance L from the distal end surface 30a of the distal portion 30, and a distance in focus by the left imaging unit 50L and the right imaging unit 50R is assumed.

When left and right images captured by the left imaging unit 50L and the right imaging unit 50R are displayed as a 3D image on the screen of the 3D display device 18, the reference plane RP indicates a position of the object point recognized to be present at a position on the screen. That is, the object point on the reference plane RP is displayed so as to be present on the screen in the 3D image. In addition, it is preferable that the distance L of the reference plane RP from the distal end surface 30a be 8 cm to 10 cm that is a focus position in a general endoscope. In addition, it is preferable that about 1 cm before and after the reference plane RP be in focus as a range of the depth of field.

In the reference plane RP, a region where the field of view range VFR and the field of view range VFL overlap each other is indicated by a field of view range 3DR from the left end of the field of view range VFR and a field of view range 3DL from the right end of the field of view range VFL. In addition, in the reference plane RP, a region of only the field of view range VFR in a region where the field of view range VFR and the field of view range VFL do not overlap each other is indicated by a field of view range 2DR from the right end of the field of view range VFR, and a region of only the field of view range VFL is indicated by a field of view range 2DL from the left end of the field of view range VFL.

In addition, in the following explanation, it is assumed that the field of view range VFR is a right full field of view range VFR, the field of view range VFL is a left full field of view range VFL, the field of view range 3DR is a right 3D field of view range 3DR, the field of view range 3DL is a left 3D field of view range 3DL, and the field of view range where the right full field of view range VFR and the left full field of view range VFL overlap each other on the reference plane RP (that is, the field of view range obtained by adding the right 3D field of view range 3DR and the left 3D field of view range 3DL) is a 3D field of view range 3DR&3DL. In addition, it is assumed that the field of view range 2DR is a right 2D field of view range 2DR and the field of view range 2DL is a left 2D field of view range 2DL.

Figure 6:
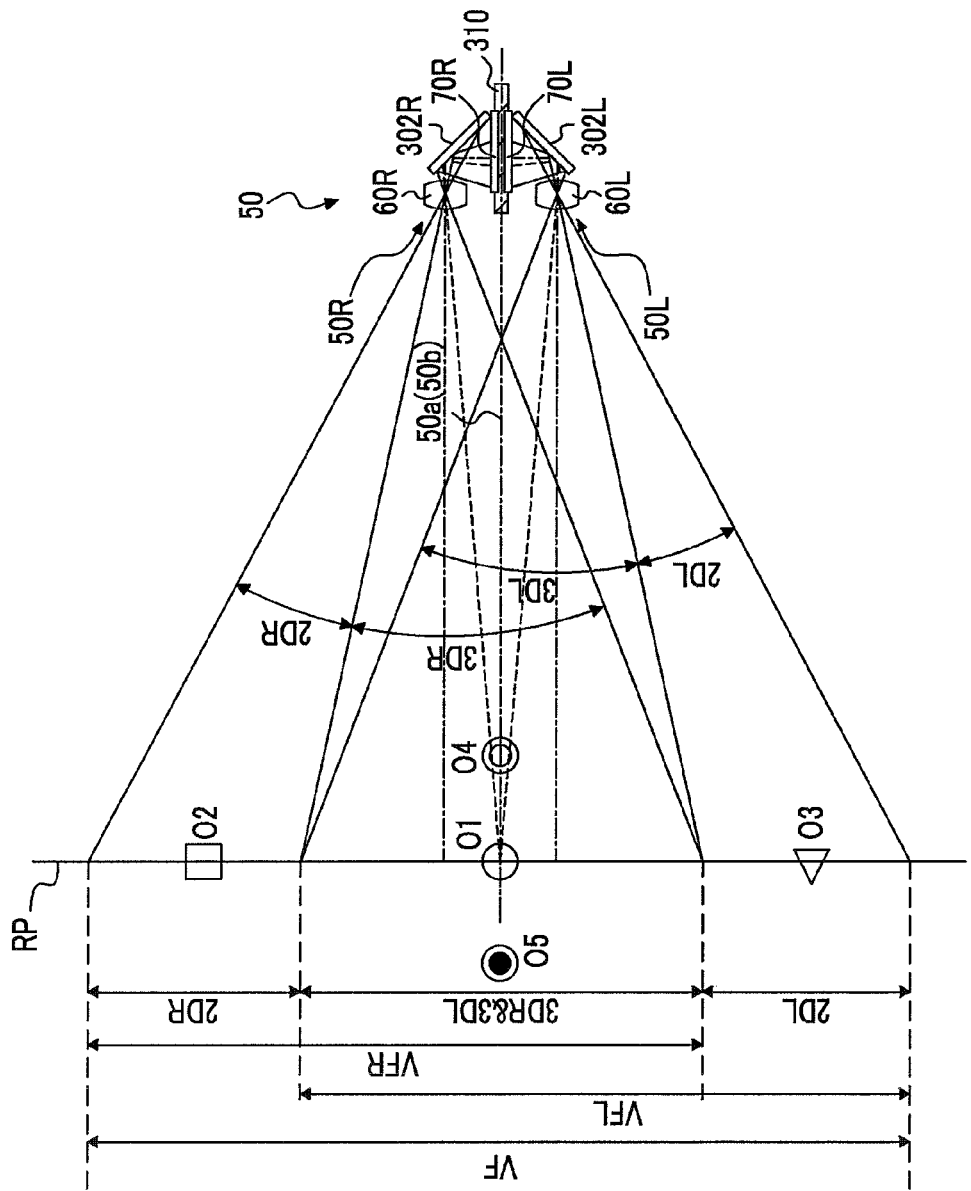
FIG. 6 is a diagram used for the explanation of display and parallax images with respect to the subject in the field of view range of the imaging units shown in FIG. 4.

Parallax images (left and right images) and display thereof when subjects O1 to O5 are present as shown in FIG. 6 in the field of view range of the imaging unit 50 configured as described above will be described. In FIG. 6, the subjects O1, O2, and O3 illustrate objects present on the reference plane RP. The subject O1 is present in the 3D field of view range 3DR&3DL, the subject O2 is present in the right 2D field of view range 2DR, and the subject O3 is present in the left 2D field of view range 2DL. The subjects O4 and O5 indicate subjects that are present in the 3D field of view range 3DR&3DL but are not present on the reference plane RP. The subject O4 is present at a position closer to the distal end surface 30a than the reference plane RP is, and the subject O5 indicates a subject present at a position farther from the distal end surface 30a than the reference plane RP is.

When the subjects O1 to O5 are present as described above, a right image IR shown in FIG. 7(A) and a left image IL shown in FIG. 7(B) are obtained as parallax images by the right imaging unit 50R and the left imaging unit 50L, respectively.

As shown in FIG. 7(A), the right image IR is configured to include an image of a right 3D image region 360R where the subject of the right 3D field of view range 3DR is reflected and an image of a right 2D image region 362R where the subject of the right 2D field of view range 2DR is reflected. In addition, images (subject images O1R, O4R, and O5R) of the subjects O1, O4, and O5 among the subjects O1 to O5 are reflected in the right 3D image region 360R, and an image (subject image O2) of the subject O2 is reflected in the right 2D image region 362R.

As shown in FIG. 7(B), the left image IL is configured to include an image of a left 3D image region 360L where the subject of the left 3D field of view range 3DL is reflected and an image of a left 2D image region 362L where the subject of the left 2D field of view range 2DL is reflected. Images (subject images O1L, O4L, and O5L) of the subjects O1, O4, and O5 among the subjects O1 to O5 are reflected in the left 3D image region 360L, and an image (subject image O3) of the subject O3 is reflected in the left 2D image region 362L.

The right image IR and the left image IL are transmitted to the processor device 14 as image data as shown in FIG. 2. By the display image generating unit 104 of the processor device 14, the right image IR is generated as an image in a right-eye display image viewed only by the right eye of the observer, and the left image IL is generated as an image in a left-eye display image viewed only by the left eye. The generated images are output to the 3D display device 18 through the display control unit 106.

Then, on the 3D display device 18, as an endoscope image, the right image IR of the right full field of view range VFR of the right imaging unit 50R is displayed so as to be viewed only by the right eye of the observer, and the left image IL of the left full field of view range VFL of the left imaging unit 50L is displayed so as to be viewed only by the left eye.

In addition, in the display image generating unit 104, the position and size of the right image IR in the right-eye display image (in the screen of the 3D display device 18) and the position and size of the left image IL in the left-eye display image (in the screen of the 3D display device 18) are adjusted, so that the image of the right 3D field of view range 3DR (image of the right 3D image region 360R) in the right image IR and the image of the left 3D field of view range 3DL (image of the left 3D image region 360L) in the left image IL are displayed so as to overlap each other on the screen of the 3D display device 18 (so as to be viewed at the overlapping position) as in an endoscope image IR&IL of FIG. 7(C).

According to this, the endoscope image IR&IL is configured to include an image of a 3D image region 360 (the right 3D image region 360R and the left 3D image region 360L) where the subject of the 3D field of view range 3DR&3DL is reflected, an image of the right 2D image region 362R where the subject of the right 2D field of view range 2DR is reflected, and an image of the left 2D image region 362L where the subject of the left 2D field of view range 2DL is reflected.

In addition, the image of the subject present in the 3D field of view range 3DR&3DL on the reference plane RP is displayed at the same position in the 3D image region 360 of the endoscope image IR&IL, as a subject image O1R&O1L shown by the addition of the subject image O1R in the right image IR and the subject image O1L in the left image IL that are images of the subject O1.

On the other hand, in the case of the image of the subject, which is present in the 3D field of view range 3DR&3DL but is present at a position closer to the distal end surface 30a than the reference plane RP is, a right-eye display image (right image IR) and a left-eye display image (left image IL) are separately displayed at different positions on the left and right sides in the 3D image region 360 of the endoscope image IR&IL, respectively, as the subject image O4R in the right image IR and the subject image O4L in the left image IL that are images of the subject O4.

On the contrary, in the case of the image of the subject, which is present in the 3D field of view range 3DR&3DL but is present at a position farther from the distal end surface 30a than the reference plane RP is, a right-eye display image (right image IR) and a left-eye display image (left image IL) are separately displayed at different positions on the right and left sides in the 3D image region 360 of the endoscope image IR&IL, respectively, as the subject image O5R in the right image IR and the subject image O5L in the left image IL that are images of the subject O5.

In addition, the image of the subject present in the right 2D field of view range 2DR, which is a region where the right full field of view range VFR and the left full field of view range VFL do not overlap each other, is displayed in only the right 2D image region 362R of the endoscope image IR&IL so as to be able to be viewed only by the right eye, as the subject image O2 in the right image IR that is an image of the subject O2 present on the reference plane RP. Similarly, the image of the subject present in the left 2D field of view range 2DL, which is a region where the right full field of view range VFR and the left full field of view range VFL do not overlap each other, is displayed in only the left 2D image region 362L of the endoscope image IR&IL so as to be able to be viewed only by the left eye, as the subject image O3 in the left image IL that is an image of the subject O3 present in the left 2D field of view range 2DL on the reference plane RP.

Therefore, by displaying the right image IR of the right full field of view range VFR, which is captured by the right imaging unit 50R, and the left image IL of the left full field of view range VFL, which is captured by the left imaging unit 50L, on the 3D display device 18 as a 3D image so that the image of the right 3D field of view range 3DR and the image of the left 3D field of view range 3DL overlap each other as shown in FIG. 7(C), the observer can view stereoscopically subjects such as the subjects O1, O4, and O5 present in the region of the 3D field of view range 3DR&3DL. The subject present on the reference plane RP, such as the subject O1, is recognized as a subject present on the screen of the 3D display device 18. The subject present at a position closer to the distal end surface 30a than the reference plane RP is, such as the subject O4, is recognized as a subject present at a position closer to the distal end surface 30a than the screen of the 3D display device 18 is. The subject present at a position farther from the distal end surface 30a than the reference plane RP is, such as the subject O5, is recognized as a subject present at a position farther from the distal end surface 30a than the screen of the 3D display device 18 is.

In addition, since a subject present in a region imaged by only one of the imaging units 50R and 50L, such as the right 2D field of view range 2DR or the left 2D field of view range 2DL, is also displayed as a 2D image, it is possible to observe the state of a subject body part in the field of view range wider than the 3D image of the 3D field of view range 3DR&3DL.

Next, the operation when moving the image sensors 70L and 70R (substrate 310) in the direction of the central axis 50b (observation axis direction) will be described.

Figure 8:
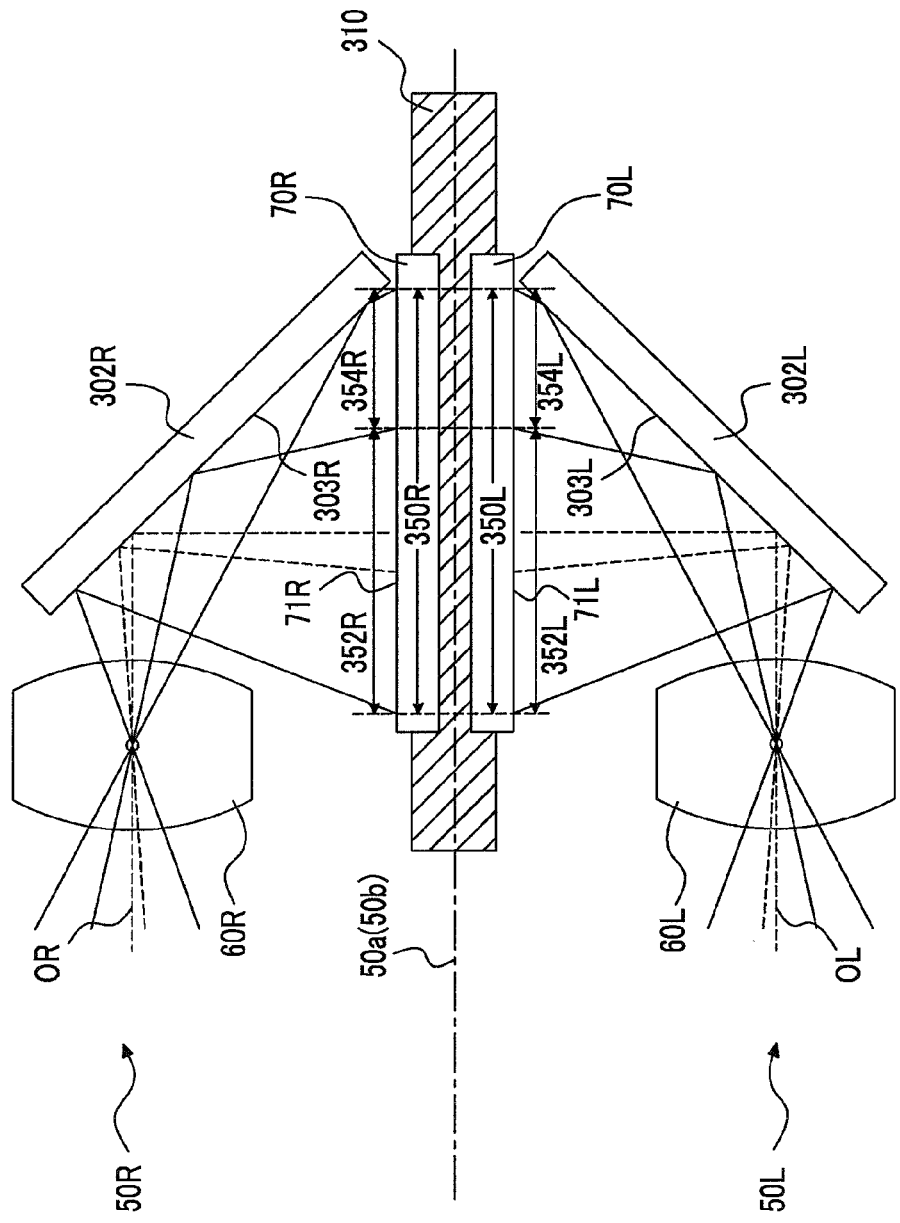
FIG. 8 is a diagram showing a state when image sensors of the imaging units shown in FIG. 4 are set at the rear end position.
Figure 9:
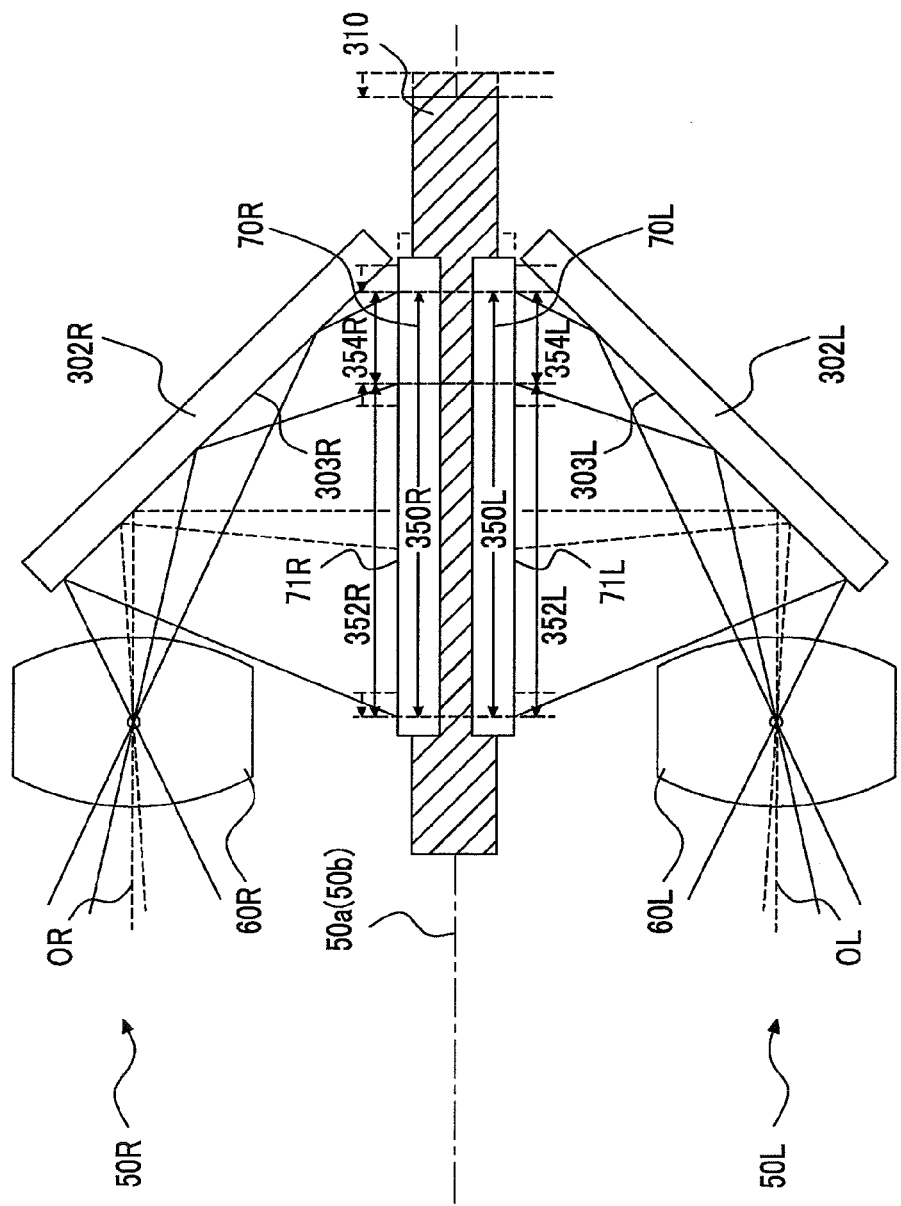
FIG. 9 is a diagram showing a state when image sensors of the imaging units shown in FIG. 4 are set at the front end position.
Figure 10:
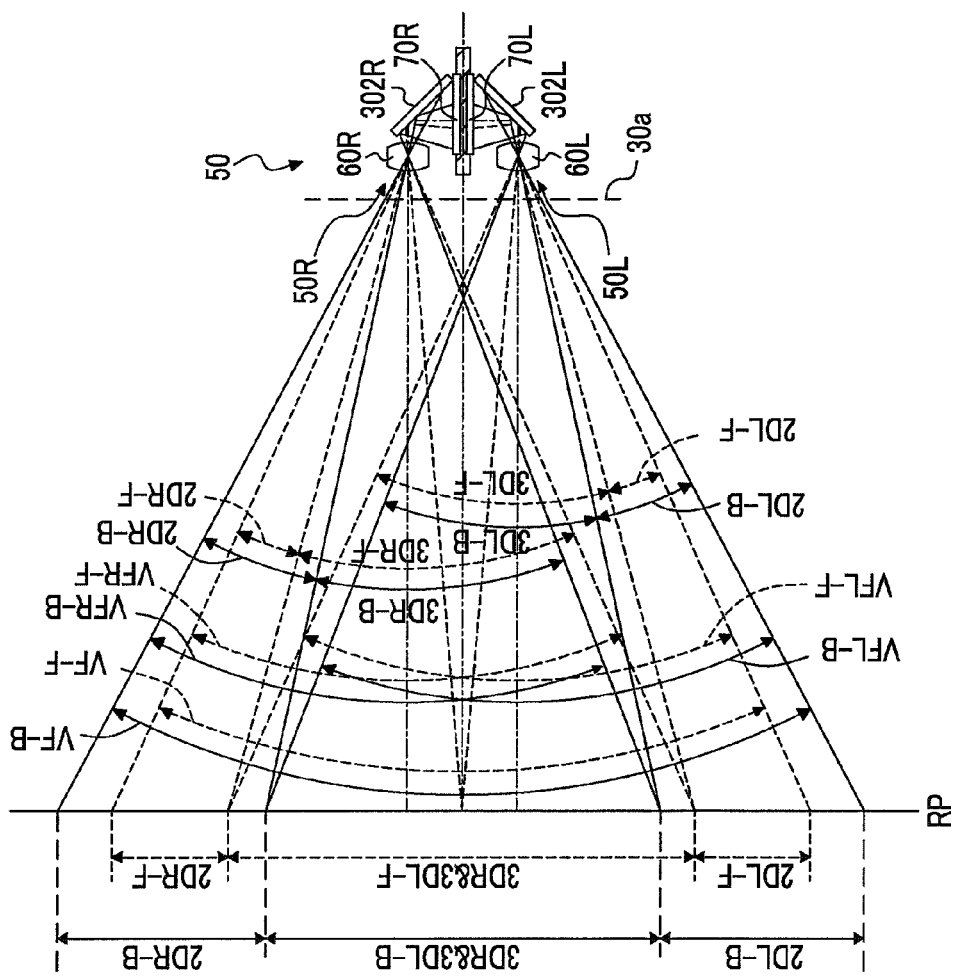
FIG. 10 is a diagram showing the field of view range in a state where the image sensors of the imaging units shown in FIG. 4 are set at the rear end position and the front end position.

FIG. 8 shows a state where each of the image sensors 70R and 70L is set at a rear end position (end position on the right side in the diagram) that is a rearmost end side (side away from the distal end surface 30a) in a direction of the central axis 50b (longitudinal axis 20a). FIG. 9 shows a state where each of the image sensors 70R and 70L is moved from the rear end position and set at a front end position (end position on the left side in the diagram) that is a foremost end side in the direction of the central axis 50b. FIG. 10 shows a state of the field of view range in the state of the rear end position and the front end position. In addition, the front lens 300 is omitted in FIGS. 8 to 10.

In FIGS. 8 and 9, assuming that ranges where the image sensors 70R and 70L capture images effectively, of subject images formed by subject light transmitted through the right imaging optical system 60R and the left imaging optical system 60L and reflected by the reflecting mirrors 302R and 302L, are ranges of the light receiving surfaces 71R and 71L, horizontal ranges of the regions of the light receiving surfaces 71R and 71L are indicated by 350R and 350L. In addition, the light receiving surfaces 71R and 71L of the image sensors 70R and 70L also have predetermined sizes in the vertical direction (direction perpendicular to the plane of the diagram in FIGS. 8 and 9) as shown in FIGS. 11(A) and 11(B) when the light receiving surfaces 71R and 71L are viewed from the front side, and the regions 350R and 350L including the horizontal and vertical ranges of the regions of the light receiving surfaces 71R and 71L are also referred to as entire regions 350R and 350L of the light receiving surfaces 71R and 71L.

When the image sensors 70R and 70L are shifted in the direction of the central axis 50b between the rear end position and the front end position by moving the substrate 310 in a direction along the central axis 50b between the rear end position in FIG. 8 and the front end position in FIG. 9 using the motor 320 shown in FIG. 4, the light receiving surfaces 71R and 71L of the image sensors 70R and 70L are also shifted in the direction of the central axis 50b.

Each field of view range of the imaging units 50R and 50L is also shifted in the left and right direction (horizontal direction and direction perpendicular to the central axis 50b) with the shift of the light receiving surfaces 71R and 71L in the direction of the central axis 50b.

In FIG. 10, the imaging unit 50 is shown in the same manner as that shown in FIG. 5, and a position as the reference plane RP is shown. In a state where the image sensors 70R and 70L are set at rear end positions as shown in FIG. 8, the full field of view range VF of the imaging unit 50 is a full field of view range VF-B, the right full field of view range VFR, the right 3D field of view range 3DR, and the right 2D field of view range 2DR in the right imaging unit 50R are a right full field of view range VFR-B, a right 3D field of view range 3DR-B, and a right 2D field of view range 2DR-B, the left full field of view range VFL, the left 3D field of view range 3DL, and the left 2D field of view range 2DL in the left imaging unit 50L are a left full field of view range VFL-B, a left 3D field of view range 3DL-B, and a left 2D field of view range 2DL-B, and the 3D field of view range 3DR&3DL in the reference plane RP is a 3D field of view range 3DR&3DL-B.

On the other hand, in a state where the image sensors 70R and 70L are set at front end positions as shown in FIG. 9, the full field of view range VF of the imaging unit 50 is a full field of view range VF-F, the right full field of view range VFR, the right 3D field of view range 3DR, and the right 2D field of view range 2DR in the right imaging unit 50R are a right full field of view range VFR-F, a right 3D field of view range 3DR-F, and a right 2D field of view range 2DR-F, the left full field of view range VFL, the left 3D field of view range 3DL, and the left 2D field of view range 2DL in the left imaging unit 50L are a left full field of view range VFL-F, a left 3D field of view range 3DL-F, and a left 2D field of view range 2DL-F, and the 3D field of view range 3DR&3DL in the reference plane RP is a 3D field of view range 3DR&3DL-F.

According to this, when the image sensors 70R and 70L are shifted to the front side in the direction of the central axis 50b from the rear end position in FIG. 8 to the front end position in FIG. 9, the right full field of view range VFR is shifted from the right side to the left side as a whole, and the left full field of view range VFL is shifted from the left side to the right side as a whole. That is, when the image sensors 70R and 70L are shifted in the direction of the central axis 50b, the right full field of view range VFR and the left full field of view range VFL are shifted in the opposite directions of the left and right directions. In addition, in this case, since there is no shift of the right full field of view range VFR and the left full field of view range VFL in the vertical direction (direction perpendicular to the plane of the diagram), explanation regarding each field of view range will also be omitted below.

Therefore, the full field of view range VF of the imaging unit 50 becomes wide in the left and right direction as the setting positions of the image sensors 70R and 70L become close to the rear end position, and the full field of view range VF of the imaging unit 50 becomes narrow in the left and right directions as the setting positions of the image sensors 70R and 70L become close to the front end position.

In addition, the width of the 3D field of view range 3DR&3DL (the right 3D field of view range 3DR and the left field of view range 3DL) in the left and right direction decreases as the setting positions of the image sensors 70R and 70L become close to the rear end position, and the width of the 3D field of view range 3DR&3DL (the right 3D field of view range 3DR and the left field of view range 3DL) in the left and right directions increases as the setting positions of the image sensors 70R and 70L become close to the front end position.

On the other hand, the widths of the right 2D field of view range 2DR and the left 2D field of view range 2DL in the left and right direction increase as the setting positions of the image sensors 70R and 70L become close to the rear end position, and the widths of the right 2D field of view range 2DR and the left 2D field of view range 2DL in the left and right directions decrease as the setting positions of the image sensors 70R and 70L become close to the front end position.

Figure 11:
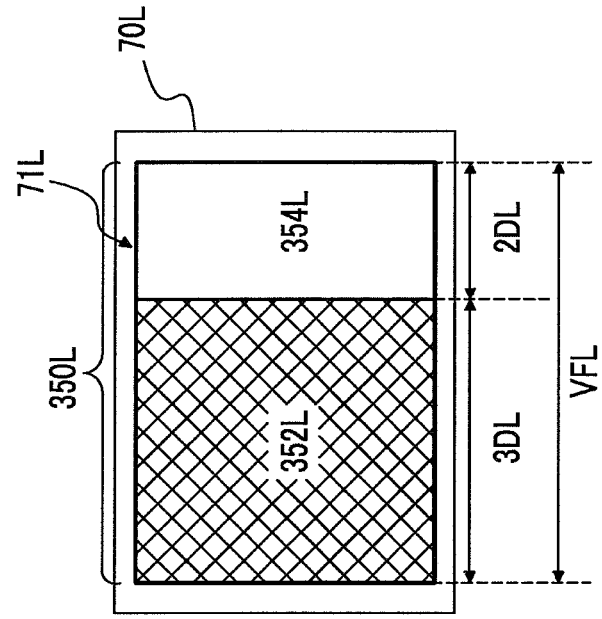
FIG. 11 is a diagram of the image sensors of the imaging units when viewed from the front side.
Figure 11:
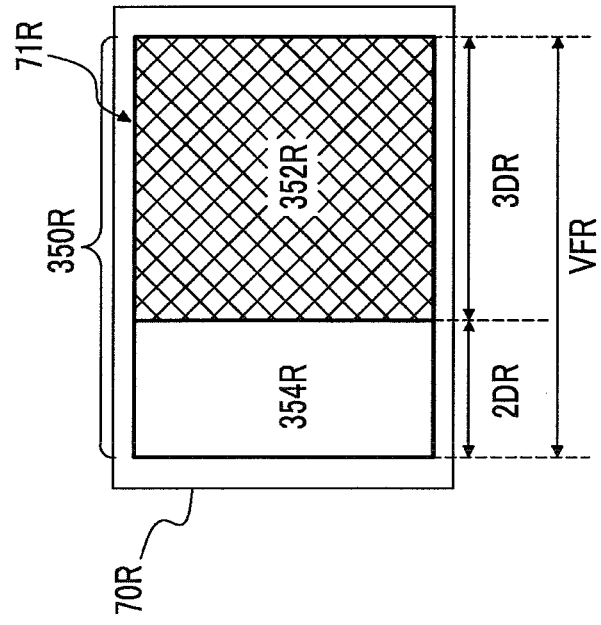

In FIGS. 8 and 9, in the entire regions 350R and 350L of the light receiving surfaces 71R and 71L of the image sensors 70R and 70L, regions where subject images of the right 3D field of view range 3DR (3DR-B, 3DR-F), the right 2D field of view range 2DR (2DR-B, 2DR-F), the left 3D field of view range 3DL (3DL-B, 3DR-F), and the left 2D field of view range 2DL (2DL-B, 2DL-F) are acquired as images are indicated by 352R, 354R, 352L, and 354L. FIG. 11 shows these regions when viewed from the front side.

In addition, the regions 352R and 352L are referred to as a right 3D region 352R and a left 3D region 352L, respectively, and the regions 354R and 354L are referred to as a right 2D region 354R and a left 2D region 354L, respectively.

As shown in FIGS. 8 and 9, the entire regions 350R and 350L of the light receiving surfaces 71R and 71L are shifted to positions on the rear side in the direction of the central axis 50b as the setting positions of the image sensors 70R and 70L become close to the rear end position, and the entire regions 350R and 350L of the light receiving surfaces 71R and 71L are shifted to positions on the front side in the direction of the central axis 50b as the setting positions of the image sensors 70R and 70L become close to the front end position. "The entire regions 350R and 350L of the light receiving surfaces 71R and 71L are shifted to positions on the rear or front side in the direction of the central axis 50b" is equivalent to "the image sensor 70R is shifted to the left or right side in the horizontal direction and accordingly the light receiving surface 71R is shifted to the left or right side in the horizontal direction in FIG. 11(A)" and "the image sensor 70L is shifted to the right or left side (opposite direction to the image sensor 70R) in the horizontal direction and accordingly the light receiving surface 71L is shifted to the right or left side (opposite direction to the light receiving surface 71R) in the horizontal direction in FIG. 11(B)". In addition, the shift amounts (sizes of the shift from a predetermined reference position) of the image sensors 70R and 70L and the light receiving surfaces 71R and 71L are equal.

In addition, as the setting positions of the image sensors 70R and 70L become close to the rear end position as described above by shifting the light receiving surfaces 71R and 71L in the horizontal direction in such a manner, the right full field of view range VFR is shifted rightward and the left full field of view range VFL is shifted leftward. In addition, as the setting positions of the image sensors 70R and 70L become close to the rear end position due to the shift of the right full field of view range VFR and the left full field of view range VFL in the left and right direction, the ratio of each horizontal width of the right 3D region 352R and the left 3D region 352L in the entire regions 350R and 350L of the light receiving surfaces 71R and 71L decreases, and the ratio of each horizontal width of the right 2D region 354R and the left 2D region 354L in the entire regions 350R and 350L of the light receiving surfaces 71R and 71L increases.

On the contrary, as the setting positions of the image sensors 70R and 70L become close to the front end position, the ratio of each horizontal width of the right 3D region 352R and the left 3D region 352L in the entire regions 350R and 350L of the light receiving surfaces 71R and 71L decreases, and the ratio of each horizontal width of the right 2D region 254R and the left 2D region 254L in the entire regions 350R and 350L of the light receiving surfaces 71R and 71L increases.

Figure 12:
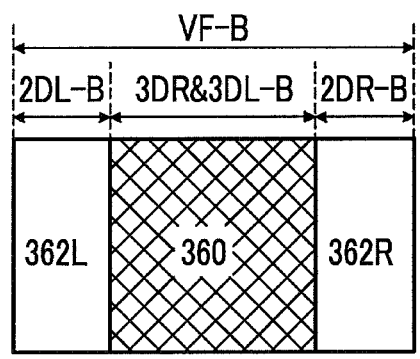
FIG. 12 is a diagram showing the image regions of a right image and a left image, which are acquired by a right imaging unit and a left imaging unit, and their display positions at the time of 3D display in a state where image sensors are set to the rear end position as in FIG. 8.
Figure 12:
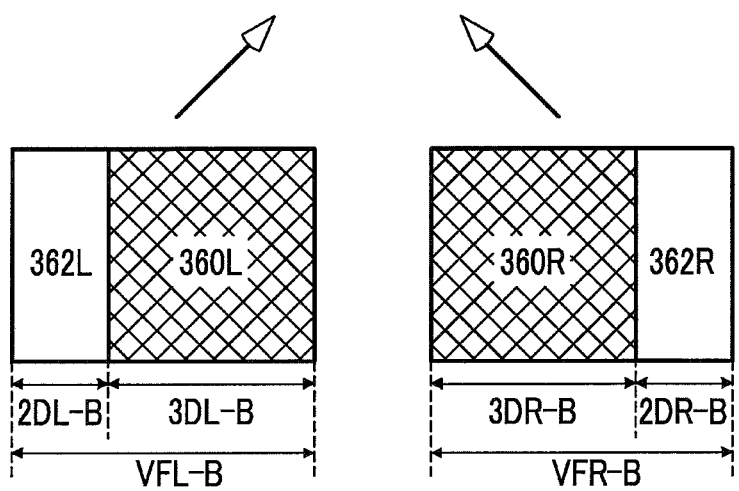
Figure 13:
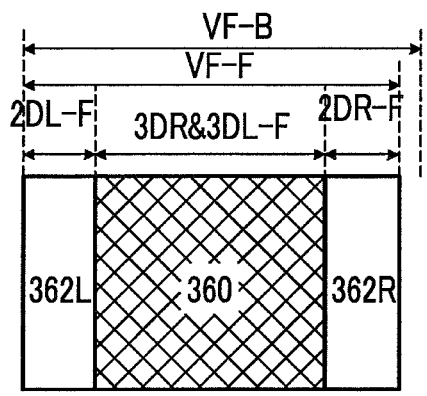
FIG. 13 is a diagram showing the image regions of a right image and a left image, which are acquired by a right imaging unit and a left imaging unit, and their display positions at the time of 3D display in a state where image sensors are set to the front end position as in FIG. 9.
Figure 13:
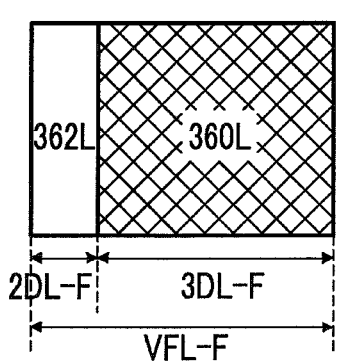
Figure 13:
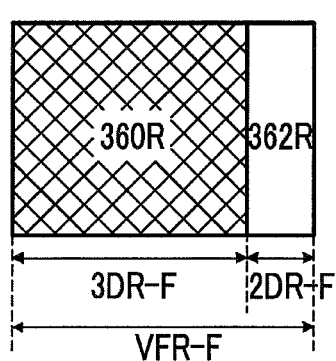

FIGS. 12(A) and 12(B) show image regions of the right image IR and left image IL acquired by the right imaging unit 50R and the left imaging unit 50L in a state where the image sensors 70R and 70L are set at the rear end position as in FIG. 8, and FIGS. 13(A) and 13(B) show image regions of the right image IR and left image IL acquired by the right imaging unit 50R and the left imaging unit 50L in a state where the image sensors 70R and 70L are set at the front end position as in FIG. 9.

Figure 7:
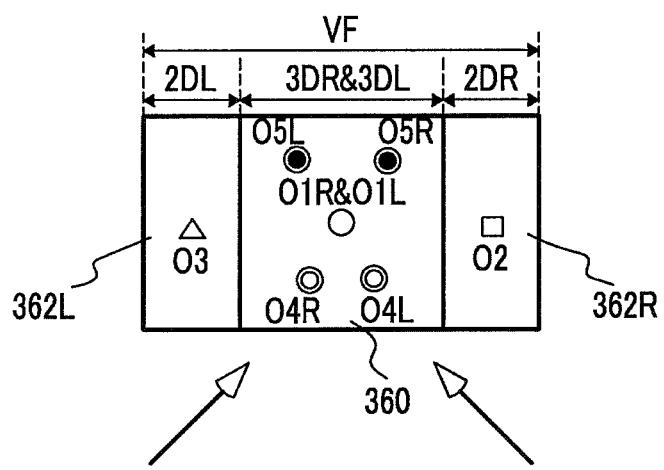
FIG. 7 is a diagram illustrating a right image and a left image captured as parallax images by a right imaging unit and a left imaging unit.
Figure 7:
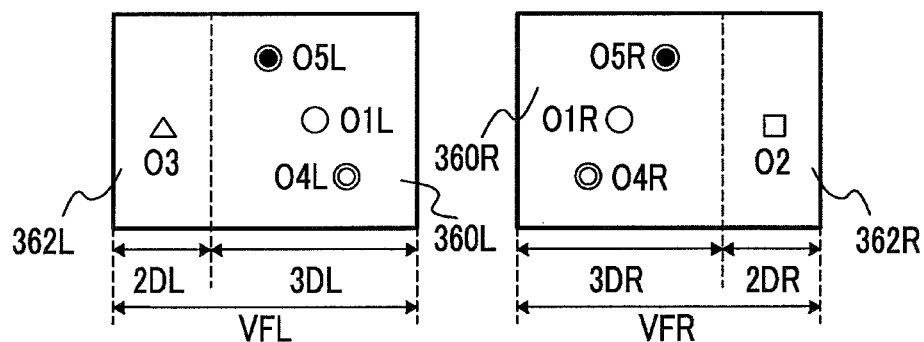

As also shown in FIG. 7, in FIGS. 12(A) and 13(A), in the image region of the right image IR acquired by the right imaging unit 50R, the right 3D image region 360R indicates an image region which is imaged by the right 3D region 352R (refer to FIG. 11(A)) of the light receiving surface 71R and in which the subject of the right 3D field of view range 3DR (3DR-B, 3DR-F) is reflected, and the right 2D image region 362R indicates an image region which is imaged by the right 2D region 354R (refer to FIG. 11(A)) of the light receiving surface 71R and in which the subject of the right 2D field of view range 2DR (2DR-B, 2DR-F) is reflected.

Similarly, in FIGS. 12(B) and 13(B), in the image region of the left image IL acquired by the left imaging unit 50L, the left 3D image region 360L indicates an image region which is imaged by the left 3D region 352L (refer to FIG. 11(B)) of the light receiving surface 71L and in which the subject of the left 3D field of view range 3DL (3DL-B, 3DL-F) is reflected, and the left 2D image region 362L indicates an image region which is imaged by the left 2D region 354L (refer to FIG. 11(B)) of the light receiving surface 71L and in which the subject of the left 2D field of view range 2DL (2DL-B, 2DL-F) is reflected.

As shown in these diagrams, as the setting positions of the image sensors 70R and 70L become close to the rear end position, the horizontal widths of the right 3D image region 360R and the left 3D image region 360L in the right image IR and the left image IL decrease, and the horizontal widths of the right 2D image region 362R and the left 2D image region 362L in the right image IR and the left image IL increase.

On the contrary, as the setting positions of the image sensors 70R and 70L become close to the front end position, the horizontal widths of the right 3D image region 360R and the left 3D image region 360L in the right image IR and the left image IL increase, and the horizontal widths of the 2D image regions 362R and 362L in the right image IR and the left image IL decrease.

Accordingly, when the right image IR and the left image IL are displayed on the 3D display device 18 as the endoscope image IR&IL as shown in FIGS. 12(C) and 13(C) such that the image of the right 3D image region 360R of the right image IR and the image of the left 3D image region 360L of the left image IL overlap each other, as the setting positions of the image sensors 70R and 70L become close to the rear end position, the horizontal width of the 3D image region 360 where the subject of the 3D field of view range 3DR&3DL is reflected and displayed as a 3D image decreases, and the horizontal widths of the right 2D image region 362R and the left 2D image region 362L where the subjects of the right 2D field of view range 2DR and the left 2D field of view range 2DL are reflected and displayed as 2D images increase.

On the contrary, as the setting positions of the image sensors 70R and 70L become close to the front end position, the horizontal width of the 3D image region 360 increases, and the horizontal widths of the right 2D image region 362R and the left 2D image region 362L decrease.

In addition, the horizontal width of the entire image region from the right end of the right 2D image region 362R of the endoscope image IR&IL to the left end of the left 2D image region 362L, that is, the horizontal width of the entire image region where the subject of the full field of view range VF of the imaging unit 50 is reflected increases with an increase in the full field of view range VF in the horizontal direction (left and right direction) as the setting positions of the image sensors 70R and 70L become close to the rear end position, and decreases with a decrease in the full field of view range VF in the horizontal direction (left and right direction) as the setting positions of the image sensors 70R and 70L become close to the front end position.

In addition, when the right image IR and the left image IL are displayed on the 3D display device 18 as the endoscope image IR&IL as shown in FIGS. 12(C) and 13(C) such that the image of the right 3D image region 360R of the right image IR and the image of the left 3D image region 360L of the left image IL overlap each other, the sizes (horizontal widths) of the right 3D image region 360R in the right image IR and the left 3D image region 360L in the left image IL change with the setting positions of the image sensors 70R and 70L in the direction of the central axis 50b.

Therefore, when displaying the endoscope image IR&IL on the 3D display device 18 as shown in FIGS. 12(C) and 13(C) using the right image IR and left image IL, the size (width) of the 3D image region 360 displayed as a 3D image, that is, the sizes (horizontal widths) of image regions recognized as the right image region 360R of the right image IR and the left image region 360L of the left image IL need to be changed according to the setting positions of the image sensors 70R and 70L in the direction of the central axis 50b.

Therefore, data regarding the sizes (horizontal widths) of the right 3D image region 360R and the left 3D image region 360L for the setting positions of the image sensors 70R and 70L in the direction of the central axis 50b is generated in advance and is stored in storage means so that the data can be referred to by the display image generating unit 104 (refer to FIG. 2) that generates the endoscope image IR&IL. The storage means may be a storage medium built in the processor device 14, or may be a storage medium that can be attached to or detached from the processor device 14. In addition, the storage means may be a storage medium built in the endoscope 12.

In addition, when generating the endoscope image IR&IL in the display image generating unit 104, it is preferable to acquire the information of the setting positions of the image sensors 70R and 70L in the direction of the central axis 50b and to change the sizes (horizontal widths) of image regions, which are recognized as the right 3D image region 360R in the right image IR and the left 3D image region 360L in the left image IL, according to the setting positions of the image sensors 70R and 70L in the direction of the central axis 50b with reference to the data stored in the storage means. The acquisition of the information of the setting positions of the image sensors 70R and 70L in the direction of the central axis 50b can be performed by acquiring information from position detection means for detecting the setting positions of the image sensors 70R and 70L in the direction of the central axis 50b, information from the control unit 322 shown in FIG. 4 (information of the position to control the image sensors 70R and 70L (substrate 310) in the direction of the central axis 50b), or instruction information (information indicating the positions of the image sensors 70R and 70L) input through the operating unit 324. In addition, in a configuration where the setting positions of the image sensors 70R and 70L (substrate 310) are determined by the operating member of the operating unit 22 of the endoscope 12 through the operating wire, the information of the setting positions of the image sensors 70R and 70L in the direction of the central axis 50b can also be acquired by acquiring information from detection means for detecting the operating position of the operating member.

According to the configuration and function of the imaging unit 50 described above, it is possible to acquire a 3D image suitable for precise observation, for example, when observing a lesion part or when treating a part to be treated using a treatment instrument and a 2D image suitable for the observation of a wide field of view range, for example, at the time of orienting when guiding an endoscope or a treatment instrument to a part to be treated or the like or when checking the treatment situation or the like.

In addition, since the widths of the full field of view range VF of the imaging unit 50 and the 3D field of view range 3DR&3DL in the left and right direction can be changed by shifting the setting positions of the image sensors 70R and 70 in the direction of the central axis 50b, changes to an appropriate field of view range can be made according to the situation.

For example, when observing a lesion part or when treating a part to be treated using a treatment instrument, the width (angle range) of the full field of view range VF of the imaging unit 50 in the left and right direction is reduced, but the width (angle range) of the 3D field of view range 3DR&3DL in the left and right direction can be increased by setting the image sensors 70R and 70L at the front end position (or the neighborhood). As a result, since a subject body part can be captured as a 3D image having a wide field of view range in the left and right direction, the subject body part can be accurately observed by the 3D image.

On the other hand, for example, at the time of orienting when guiding an endoscope or a treatment instrument to a part to be treated or the like or when checking the treatment situation, the width (angle range) of the 3D field of view range 3DR&3DL is reduced, but the width (angle range) of the full field of view range VF of the imaging unit 50 in the left and right direction can be increased by setting the image sensors 70R and 70L at the rear end position (or the neighborhood). As a result, since a subject body part having a wide field of view range in the left and right direction can be captured as the entire image including not only the 3D image of the central portion but also the 2D images on the left and right sides of the 3D image, observation in a wide field of view range can be performed by the entire image.

In addition, since the field of view range of the imaging unit 50 is changed by shifting the image sensors 70R and 70L integrally in the direction of the central axis 50b instead of shifting the image sensors 70R and 70L separately, the configuration is simple. As a result, it is possible to suppress an increase in the size of the distal portion 30 of the endoscope 12.

As described above, in the configuration of the imaging unit 50 of the above embodiment, as shown in FIG. 4, subject light transmitted through the right imaging optical system 60R and the left imaging optical system 60L are reflected toward the central plane 50a (central axis 50b) by the reflecting mirror 302R and the reflecting mirror 302L of the right imaging unit 50R and the left imaging unit 50L, and the image sensors 70R and 70L are fixed to the substrate 310 back to back along the central plane 50a so that the light receiving surfaces 71R and 71L are disposed in the opposite directions. However, the present invention is not limited thereto.

Figure 14:
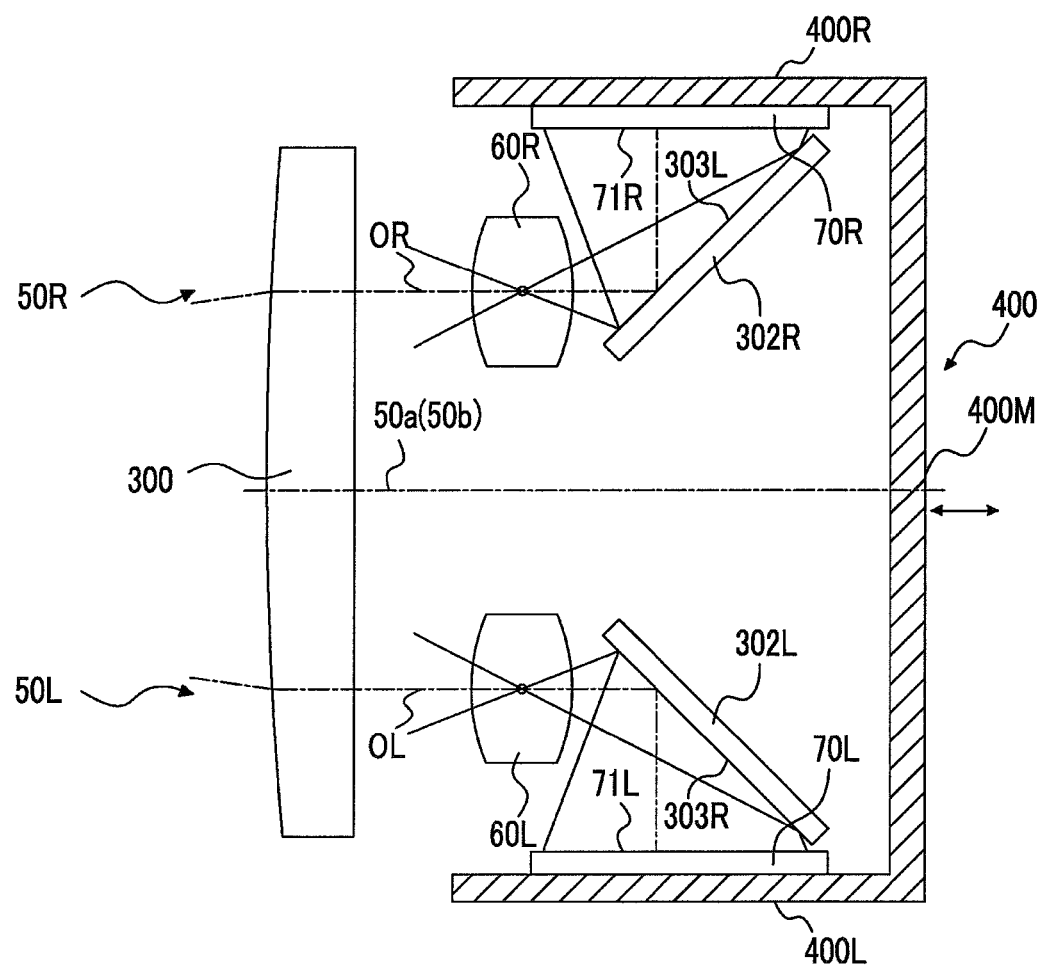
FIG. 14 is a cross-sectional view showing the configuration of another embodiment of the imaging unit in the endoscope.

FIG. 14 is a cross-sectional view showing the configuration of another embodiment of the imaging unit 50. In addition, the same reference numerals as in FIG. 4 are given to constituent components having the same or similar functions as in the imaging unit 50 of FIG. 4, and only the differences between the present embodiment and the embodiment shown in FIG. 4 will be described. In FIG. 14, the normal of each of the reflecting surfaces 303R and 303L of the reflecting mirrors 302R and 302L is parallel to the horizontal plane (plane of the diagram). In addition, the normal of the reflecting surface 303R is disposed at an angle of 45° clockwise with respect to the optical axis OR of the right imaging optical system 60R, and the normal of the reflecting surface 303L is disposed at an angle of 45° counterclockwise with respect to the optical axis OL of the left imaging optical system 60L.

By these reflecting mirrors 302R and 302L, the optical axis OR of the right imaging optical system 60R is bent in a direction perpendicular to the central plane 50a toward the opposite side to the central plane 50a, and the optical axis OL of the left imaging optical system 60L is bent in a direction perpendicular to the central plane 50a toward the opposite side to the central plane 50a. In addition, subject light transmitted through each of the right imaging optical system 60R and the left imaging optical system 60L is reflected toward the opposite side to the central plane 50a.

The image sensors 70R and 70L are respectively mounted on plate-shaped parallel portions 400R and 400L disposed in parallel to the central plane 50a of a substrate 400. Therefore, the image sensors 70R and 70L are fixed to the substrate 400 in a state where the light receiving surfaces 71R and 71L face each other.

In addition, the image sensors 70R and 70L are disposed in a manner such that the light receiving surfaces 71R and 71L are parallel to the central plane 50a, and are also disposed in a manner such that the horizontal direction of the light receiving surfaces 71R and 71L is parallel to the horizontal plane (plane of the diagram) and the vertical direction of the light receiving surfaces 71R and 71L is a direction perpendicular to the horizontal plane (direction perpendicular to the plane of the diagram). In addition, the light receiving surfaces 71R and 71L are disposed at the same distance on the opposite sides with respect to the central plane 50a.

Accordingly, the subject light transmitted through the right imaging optical system 60R and the left imaging optical system 60L and reflected toward the opposite side to the central plane 50a by the reflecting mirrors 302R and 302L forms subject images on the light receiving surfaces 71R and 71L of the image sensors 70R and 70L, and these subject images are captured by the image sensors 70R and 70L.

The substrate 400 has a function equivalent to the substrate 310 in the imaging unit 50 of FIG. 4, and is integrally formed by the parallel portions 400R and 400L, on which the image sensors 70R and 70L are mounted, and a connecting portion 400M that connects the parallel portions 400R and 400L to each other. In addition, within the distal portion 30, the substrate 400 is supported so as to be movable in the direction of the central axis 50b (direction of the longitudinal axis 20a of the insertion unit 20), and is moved in the direction of the central axis 50b by a motor or an operating wire (not shown) in the same manner as the substrate 310 in the imaging unit 50 in FIG. 4. In addition, although the substrate 400 is shown as one member in FIG. 14, the substrate 400 may have a configuration in which a plurality of members are connected to each other.

Through the above configuration, the substrate 400 and the image sensors 70R and 70L can be moved as a unit in the direction of the central axis 50b similar to the configuration of the imaging unit 50 shown in FIG. 4. Accordingly, the light receiving surfaces 71R and 71L can be shifted in the horizontal direction to change the field of view range of the imaging unit 50.

In addition, the imaging unit 50 is not limited to the configuration shown in FIG. 4 or FIG. 14, and may have the following configuration.

That is, the image sensors 70R and 70B are integrally supported by a support member so as to be movable in the direction of the central axis 50b, and the light receiving surfaces 71R and 71L of the image sensors 70R and 70B are disposed so as to be parallel to the central axis 50b and be symmetrical with respect to the central axis 50b. In addition, the optical paths of the right imaging optical system 60R and the left imaging optical system 60L are changed so as to face in the directions of the light receiving surfaces 71R and 71L by optical path change means using a reflector, such as a reflecting mirror or a prism, so that image surfaces on which subject images are formed by the right imaging optical system 60R and the left imaging optical system 60L become the positions of the light receiving surfaces 71R and 71L. Accordingly, by moving the image sensors 70R and 70L using the support member, the light receiving surfaces 71R and 71L can be shifted in horizontally different directions as in the embodiment described above. In addition, preferably, the light receiving surfaces 71R and 71L are disposed in a manner such that the horizontal directions thereof are parallel to the left and right direction of each subject image and the directions of the left and right are opposite each other. However, since the left and right direction of each image acquired by the image sensors 70R and 70L and the directions of the left and right can be arbitrarily changed by image processing regardless of the directions of the light receiving surfaces 71R and 71L, the directions of the light receiving surfaces 71R and 71L (direction of the image sensors 70R and 70L) are not limited thereto.

As described above, in the display form of the endoscope image in the above embodiment, the composite endoscope image IR&IL of a 3D image and 2D images is displayed as shown in FIGS. 7(C), 12(C), and 13(C) using the right image IR and the left image IL acquired by the imaging unit 50. However, the display form of the endoscope image is not limited thereto. Processing regarding the display form of the endoscope image shown below can correspond to the processing of the display image generating unit 104 in the processor device 14 shown in FIG. 2.

For example, in FIGS. 7(C), 12(C), and 13(C), the image (images of the right 3D image region 360R of the right image IR and the left 3D image region 360L of the left image IL) of only the 3D image region 360 (3D field of view range 3DR&3DL) may be displayed on the 3D display device 18 as an endoscope image of only the 3D image.

In addition, on the screen of the 3D display device 18, an entire image (entire image of the full field of view range VF of the endoscope 12) including the image of the 3D image region 360 (3D field of view range 3DR&3DL) and the image of the right 2D image region 362R (right 2D field of view range 2DR) and the image of the left 2D image region 362L (left 2D field of view range 2DL), which are located on both sides of the 3D image region 360 in the horizontal direction, may be displayed as an endoscope image of only the 2D image so as to be switchable by a predetermined operation or in parallel for an endoscope image of only the 3D image (or a composite endoscope image of a 3D image and 2D images).

As a form of displaying a 3D image of the 3D image region 360 as a 2D image, it is possible to adopt a form in which the image of the right 3D image region 360R of the right image IR and the image of the left 3D image region 360L of the left image IL are thinned out to reduce resolution so that they cannot be recognized as a 3D image (3D image that cannot be viewed stereoscopically is formed), a form in which only one of the image of the right 3D image region 360R and the image of the left 3D image region 360L is displayed as an image of the 3D image region 360, or a form in which a 2D image (2D image after combination processing) is generated by combining the image of the right 3D image region 360R and the image of the left 3D image region 360L and is displayed as an image of the 3D image region 360. As a composite 2D image of the image of the right 3D image region 360R and the image of the left 3D image region 360L, for example, a form of generating an image (average image) in which these images overlap each other can be considered.

In addition, when displaying the 2D image on the 3D display device 18, the same 2D image may be displayed as a right-eye display image and a left-eye display image, or the 2D image may be displayed as either one of the right-eye display image and the left-eye display image. This is the same for the 2D image of the right 2D image region 362R of the right image IR and the 2D image of the left 2D image region 362L of the left image IL when displaying the entire image of the full field of view range VF of the endoscope 12 as an endoscope image of only the 2D image. In addition, this is the same for a case where the composite endoscope image IR&IL of a 3D image and 2D images is displayed as shown in FIGS. 7(C), 12(C), and 13(C). In addition, the endoscope image of only the 2D image may also be displayed on a monitor for 2D display provided separately from a monitor for displaying the 3D image.

In addition, when displaying the composite endoscope image IR&IL of a 3D image and 2D images as shown in FIG. 7(C) or displaying the endoscope image of only the 3D image or the endoscope image of only the 2D image as described above, only an image of the partial region may be cut and displayed instead of displaying the entire region within the screen. For example, when the aspect ratio (referred to as the value of horizontal width/vertical width) of the display area to display an endoscope image on the screen is larger than the endoscope image, the horizontal width of the display area and the horizontal width of the endoscope image may be made to be equal so that an image of a partial region of the endoscope image in the vertical direction, which is located outside the display area, is not displayed.

In addition, the observer or the like may enlarge or reduce the endoscope image displayed on the screen by a predetermined operation using the operating unit 22 of the endoscope 12 or the operating unit 324 of the processor device 14. In this case, when a part of the endoscope image is located outside the display area, an image of the region of the part of the endoscope image may be cut and displayed in the display area. In this case, the operator may change the image region, which is cut from the endoscope image and is displayed in the display area, by a scroll operation or the like.

In addition, when displaying the composite endoscope image IR&IL of a 3D image and 2D images as shown in FIG. 7(C), collapse of three-dimensional recognition occurs in a boundary region of the 3D image region 360 and the right 2D image region 362R and a boundary region of the 3D image region 360 and the left 2D image region 362L. In order to reduce the collapse, it is preferable to reduce the sudden leap from the 3D image to the 2D image by performing a thinning process or the like on the images of these boundary regions.

Figure 15:
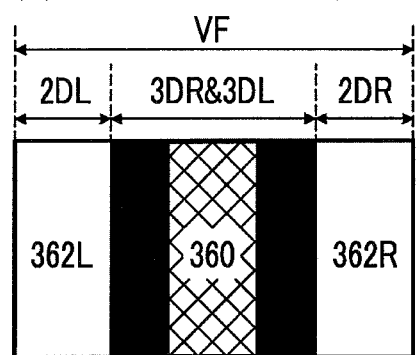
FIG. 15 is a diagram used for the explanation of a process when reducing the brightness in a boundary region between a 3D image and a 2D image.
Figure 15:
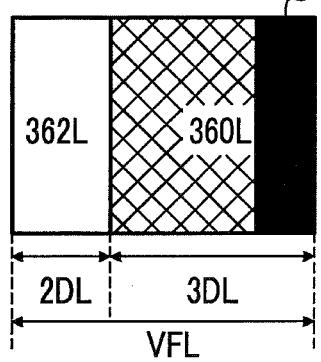
Figure 15:
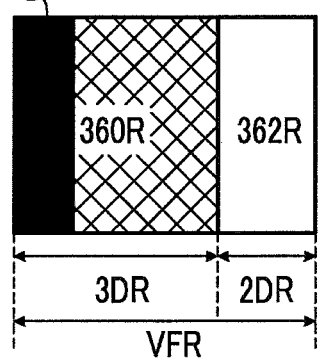

For example, a process for reducing the brightness of the images of boundary regions 420R and 420L is performed by performing a thinning process or a blurring process on the image of the boundary region 420R on the left end side of the right 3D image region 360R of the right image IR shown in FIG. 15(A) and the image of the boundary region 420L on the right end side of the left 3D image region 360L of the left image IL shown in FIG. 15(B), thereby displaying the endoscope image IR&IL as shown in FIG. 15(C). In this case, the effect of reducing the brightness by performing a thinning process, a blurring process, or the like on the images of the boundary region 420R of the right image IR and the boundary region 420L of the left image IL may be uniformly given, or the effect of reducing the brightness by the thinning process, the blurring process, or the like may be gradually strengthen as being closer to the boundary (as being closer to the left end for the image of the boundary region 420R of the right image IR and as being closer to the right end for the image of the boundary region 420L of the left image IL).

In addition, a process for reducing the brightness may be performed on the boundary region on the left end side of the left 3D image region 360L of the left image IL together with the boundary region 420R of the right image IR or instead of the boundary region 420R, and a process for reducing the brightness may be performed on the boundary region on the right end side of the right 3D image region 360R of the right image IR together with the boundary region 420L of the left image IL or instead of the boundary region 420L. In addition, this process can be similarly applied when displaying the endoscope image of only the 3D image.

Although the image sensors 70R and 70L can be set at arbitrary positions between the front end position shown in FIG. 9 and the rear end position shown in FIG. 8 in the embodiment described above, the image sensors 70R and 70L may be set at only one of the rear end position and the front end position, or may be set at a plurality of discrete positions between the front end position and the rear end position.

In addition, although the case where the present invention is applied to the flexible endoscope 12 has been described in the above embodiment, the present invention can also be applied to a hard endoscope and the like regardless of the type of the endoscope.

What is claimed is:

1. A stereoscopic endoscope device that has an imaging optical system, which forms a subject in a direction of an observation axis that is an observation direction of the subject, as a subject image, along left and right optical paths disposed symmetrically with respect to the observation axis and that acquires a pair of left and right parallax images for stereoscopic viewing, the stereoscopic endoscope device comprising:
   an imaging system that includes a pair of left and right imaging elements that have light receiving surfaces, on which images are formed by the imaging optical system, and are integrally movable along the direction of the observation axis, the light receiving surfaces of the pair of left and right imaging elements being disposed in parallel to the observation axis and symmetrically with respect to the observation axis;
   an optical path change unit which changes an optical path so that the pair of left and right optical paths face the light receiving surfaces of the pair of left and right imaging elements, respectively; and
   a field of view range change unit which shifts a field of view range of each of the pair of left and right imaging elements in a left and right direction by moving the pair of left and right imaging elements along the direction of the observation axis.

2. The stereoscopic endoscope device according to claim 1,
   wherein, in the imaging system, the light receiving surfaces of the pair of left and right imaging elements are disposed in opposite directions.

3. The stereoscopic endoscope device according to claim 1,
   wherein, in the imaging system, the light receiving surfaces of the pair of left and right imaging elements are disposed so as to face each other.

4. The stereoscopic endoscope device according to claim 1,
   wherein, in the imaging system, the pair of left and right imaging elements are integrally supported by a substrate on which a circuit is mounted.

5. The stereoscopic endoscope device according to claim 2,
   wherein, in the imaging system, the pair of left and right imaging elements are integrally supported by a substrate on which a circuit is mounted.

6. The stereoscopic endoscope device according to claim 3,
   wherein, in the imaging system, the pair of left and right imaging elements are integrally supported by a substrate on which a circuit is mounted.

7. The stereoscopic endoscope device according to claim 1,
   wherein the field of view range change unit moves the pair of left and right imaging elements in the direction of the observation axis by power of a motor connected to the imaging system.

8. The stereoscopic endoscope device according to claim 2,
   wherein the field of view range change unit moves the pair of left and right imaging elements in the direction of the observation axis by power of a motor connected to the imaging system.

9. The stereoscopic endoscope device according to claim 3,
   wherein the field of view range change unit moves the pair of left and right imaging elements in the direction of the observation axis by power of a motor connected to the imaging system.

10. The stereoscopic endoscope device according to claim 4,
    wherein the field of view range change unit moves the pair of left and right imaging elements in the direction of the observation axis by power of a motor connected to the imaging system.

11. The stereoscopic endoscope device according to claim 5,
    wherein the field of view range change unit moves the pair of left and right imaging elements in the direction of the observation axis by power of a motor connected to the imaging system.

12. The stereoscopic endoscope device according to claim 1,
wherein the field of view range change unit moves the pair of left and right imaging elements in the direction of the observation axis by power transmitting an operating wire connected to the imaging system.

13. The stereoscopic endoscope device according to claim 2,
wherein the field of view range change unit moves the pair of left and right imaging elements in the direction of the observation axis by power transmitting an operating wire connected to the imaging system.

14. The stereoscopic endoscope device according to claim 3,
wherein the field of view range change unit moves the pair of left and right imaging elements in the direction of the observation axis by power transmitting an operating wire connected to the imaging system.

15. The stereoscopic endoscope device according to claim 1, further comprising:
a front lens for setting a convergence angle that is provided on a subject side of the imaging optical system.

16. The stereoscopic endoscope device according to claim 1, further comprising:
a 3D image generation unit which generates an image of a region, in which field of view ranges of the pair of left and right parallax images overlap each other, as a 3D image for stereoscopic viewing and generating an image of a region, in which the field of view ranges do not overlap each other, as a 2D image for plan view for extending left and right sides of the 3D image.

17. The stereoscopic endoscope device according to claim 16,
wherein the 3D image generation unit reduces brightness of an image in a boundary region between the 3D image and the 2D image.

18. The stereoscopic endoscope device according to claim 1, further comprising:
a 2D image generation unit which generates an image of a full field of view range of the pair of left and right parallax images as a 2D image for plan view.

19. The stereoscopic endoscope device according to claim 18,
wherein the 2D image generation unit generates an image of a region in which field of view ranges of the pair of left and right parallax images overlap each other, as a 3D image that is not stereoscopically viewable, by thinning processing.

20. The stereoscopic endoscope device according to claim 18,
wherein the 2D image generation unit generates an image of a region in which field of view ranges of the pair of left and right parallax images overlap each other, as a 2D image, by combination processing.

21. The stereoscopic endoscope device according to claim 1, the imaging system and the optical path change unit are housed in a distal portion of the stereoscopic endoscope device.

22. A stereoscopic endoscopic device that has an imaging optical system, which forms a subject in a direction of an observation axis that is an observation direction of the subject, as a subject image, along left and right optical paths disposed symmetrically with respect to the observation axis and that acquires a pair of left and right parallax images for stereoscopic viewing, the stereoscopic endoscope device comprising:
a first imaging element having a light receiving surface, on which image is formed by the imaging optical system, and being disposed in parallel to the observation axis;
a second imaging element having a light receiving surface, on which image is formed by the imaging optical system, and being disposed in parallel to the observation axis;
a first optical path change unit which changes a first optical path of one of the left and right optical paths so that the first optical path faces the first light receiving surface;
a second optical path change unit which changes a second optical path of another one of the left and right optical paths so that the second optical path faces the second light receiving surface;
an imaging system containing the first imaging element and the second imaging element, in which the light receiving surface of the first imaging element and the light receiving surface of the second imaging element are disposed symmetrically with respect to the observation axis and the first imaging element and the second imaging element are integrally movable along the direction of the observation axis with respect to the first optical path change unit and the second optical path change unit; and
a field of view range change unit which shifts a field of view range of each of the first imaging element and the second imaging element in a left and right direction by moving the first imaging element and the second imaging element along the direction of the observation axis.

* * * * *